(12) United States Patent
Burkholz et al.

(10) Patent No.: US 12,377,248 B2
(45) Date of Patent: Aug. 5, 2025

(54) VASCULAR ACCESS DEVICE ASSEMBLY FACILITATING SINGLE-HANDED PROBE ADVANCEMENT WITH A SUPPORT MEMBER

(71) Applicant: Becton, Dickinson and Company, Franklin Lakes, NJ (US)

(72) Inventors: Jonathan Karl Burkholz, Salt Lake City, UT (US); Weston F. Harding, Lehi, UT (US); Megan Scherich, Salt Lake City, UT (US); Curtis H. Blanchard, Riverton, UT (US); Yiping Ma, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 729 days.

(21) Appl. No.: 17/192,785

(22) Filed: Mar. 4, 2021

(65) Prior Publication Data

US 2021/0290914 A1 Sep. 23, 2021

Related U.S. Application Data

(60) Provisional application No. 62/993,680, filed on Mar. 23, 2020.

(51) Int. Cl.
*A61M 25/09* (2006.01)

(52) U.S. Cl.
CPC ... *A61M 25/09* (2013.01); *A61M 2025/09066* (2013.01); *A61M 2025/09116* (2013.01); *A61M 2025/09175* (2013.01)

(58) Field of Classification Search
CPC .......... A61M 2025/09116; A61M 2025/0019; A61M 2005/1587; A61M 25/09041; A61B 1/00142; A61B 1/00144
See application file for complete search history.

(56) References Cited

U.S. PATENT DOCUMENTS

| 4,417,886 | A | * | 11/1983 | Frankhouser | A61M 25/0606 604/528 |
| 5,246,426 | A | * | 9/1993 | Lewis | A61M 25/0693 604/168.01 |

(Continued)

FOREIGN PATENT DOCUMENTS

| JP | 2019509781 A | 4/2019 |
| WO | 2018175590 A1 | 9/2018 |

(Continued)

*Primary Examiner* — Nathan R Price
*Assistant Examiner* — Adam J. Cermak
(74) *Attorney, Agent, or Firm* — The Webb Law Firm

(57) ABSTRACT

An IV device assembly may include a lumen forming a fluidic channel within the IV device assembly. The lumen may be fluidically coupled to a vascular access device (VAD) coupler via a funnel coupler, and an IV device assembly coupler at a proximal end of the lumen. The IV device assembly may also include one or more of the following: a collapsible sleeve formed coaxially around a first portion of the lumen and mechanically coupled to the funnel coupler, a probe formed along a second portion of the lumen within the collapsible sleeve and into the VAD coupler, a translation handle that translates the probe out of a distal end of the VAD coupler, and a fixed grip formed around the lumen to maintain a position of the IV device assembly relative to the translation handle.

10 Claims, 21 Drawing Sheets

(56) References Cited

U.S. PATENT DOCUMENTS

| | | | | |
|---|---|---|---|---|
| 5,415,177 | A * | 5/1995 | Zadini | A61M 25/0116 600/585 |
| 5,695,474 | A * | 12/1997 | Daugherty | A61M 25/0631 604/162 |
| 5,704,914 | A * | 1/1998 | Stocking | A61M 25/0606 604/195 |
| 6,231,564 | B1 * | 5/2001 | Gambale | A61M 25/0113 604/528 |
| 6,512,957 | B1 * | 1/2003 | Witte | A61N 1/05 607/116 |
| 6,626,869 | B1 * | 9/2003 | Bint | A61M 25/09041 604/164.01 |
| 8,366,685 | B2 * | 2/2013 | Devgon | A61B 5/150511 604/173 |
| 8,676,301 | B2 * | 3/2014 | Coyle | A61M 25/0097 600/585 |
| 9,162,037 | B2 * | 10/2015 | Belson | A61M 25/09 |
| 9,186,100 | B2 * | 11/2015 | Devgon | A61B 5/1427 |
| 9,744,344 | B1 * | 8/2017 | Devgon | A61M 39/0247 |
| 9,750,446 | B2 * | 9/2017 | Devgon | A61B 5/154 |
| 10,064,576 | B2 | 9/2018 | Devgon | |
| 10,076,272 | B2 * | 9/2018 | Devgon | A61B 5/15003 |
| 10,143,411 | B2 * | 12/2018 | Cabot | A61B 5/150236 |
| 10,300,247 | B2 | 5/2019 | Devgon et al. | |
| 10,493,262 | B2 * | 12/2019 | Tran | A61M 25/0097 |
| 10,525,236 | B2 * | 1/2020 | Belson | A61B 5/150389 |
| 11,020,571 | B2 * | 6/2021 | Belson | A61M 25/09041 |
| 11,033,719 | B2 * | 6/2021 | Braithwaite | A61M 25/0631 |
| 11,123,524 | B2 * | 9/2021 | Hall | A61M 29/00 |
| 11,337,628 | B2 * | 5/2022 | Burkholz | A61M 5/3148 |
| 11,504,503 | B2 * | 11/2022 | Burkholz | A61M 25/0625 |
| 11,617,863 | B2 * | 4/2023 | DiCianni | A61M 25/065 604/159 |
| 11,931,531 | B2 * | 3/2024 | Scherich | A61M 25/09 |
| 2005/0165355 | A1 * | 7/2005 | Fitzgerald | A61M 25/0631 604/164.08 |
| 2006/0100582 | A1 * | 5/2006 | Marianowicz | A61B 17/3401 604/158 |
| 2008/0300574 | A1 * | 12/2008 | Belson | A61M 25/09 604/510 |
| 2008/0319387 | A1 * | 12/2008 | Amisar | A61M 25/0111 604/533 |
| 2010/0094310 | A1 * | 4/2010 | Warring | A61M 25/0631 606/108 |
| 2011/0071502 | A1 * | 3/2011 | Asai | A61M 25/0606 604/528 |
| 2012/0191010 | A1 * | 7/2012 | Cabot | A61B 5/150236 600/581 |
| 2012/0197200 | A1 * | 8/2012 | Belson | A61M 25/065 604/164.12 |
| 2012/0277630 | A1 * | 11/2012 | Devgon | A61B 5/1427 600/581 |
| 2013/0018359 | A1 * | 1/2013 | Coyle | A61M 25/09041 604/528 |
| 2013/0096428 | A1 * | 4/2013 | Gillies | A61M 25/01 600/434 |
| 2014/0094774 | A1 * | 4/2014 | Blanchard | A61M 25/0105 604/164.08 |
| 2014/0364766 | A1 * | 12/2014 | Devgon | A61B 5/150396 600/581 |
| 2015/0224287 | A1 * | 8/2015 | Bian | A61M 25/0606 604/218 |
| 2016/0045715 | A1 * | 2/2016 | Galgano | A61M 25/0662 604/510 |
| 2016/0121086 | A1 * | 5/2016 | Castro | A61M 25/09041 600/585 |
| 2016/0256667 | A1 * | 9/2016 | Ribelin | A61M 25/09041 |
| 2017/0120014 | A1 * | 5/2017 | Harding | A61M 25/0693 |
| 2017/0120015 | A1 * | 5/2017 | Burkholz | A61M 25/0637 |
| 2017/0216564 | A1 * | 8/2017 | Devgon | A61B 5/150816 |
| 2018/0272107 | A1 * | 9/2018 | Ehrenreich | A61B 5/15003 |
| 2018/0296799 | A1 * | 10/2018 | Horst | A61M 25/0606 |
| 2019/0021640 | A1 * | 1/2019 | Burkholz | A61B 5/15003 |
| 2019/0022367 | A1 * | 1/2019 | Burkholz | A61M 25/0618 |
| 2019/0201668 | A1 * | 7/2019 | Funk | A61B 5/15003 |
| 2019/0321590 | A1 * | 10/2019 | Burkholz | A61M 25/09041 |
| 2020/0001051 | A1 * | 1/2020 | Huang | A61M 25/0618 |
| 2020/0016374 | A1 * | 1/2020 | Burkholz | A61M 25/0606 |
| 2020/0078566 | A1 * | 3/2020 | Mitchell | A61M 25/09041 |
| 2020/0100716 | A1 * | 4/2020 | Devgon | A61M 25/0113 |
| 2020/0197682 | A1 * | 6/2020 | Franklin | A61M 25/0097 |
| 2021/0052851 | A1 * | 2/2021 | Devgon | A61M 25/0113 |
| 2021/0113816 | A1 * | 4/2021 | DiCianni | A61M 25/09041 |
| 2022/0032008 | A1 * | 2/2022 | Khoo | A61M 25/0113 |

FOREIGN PATENT DOCUMENTS

| | | |
|---|---|---|
| WO | 2018213148 A1 | 11/2018 |
| WO | 2019203997 A2 | 10/2019 |

* cited by examiner

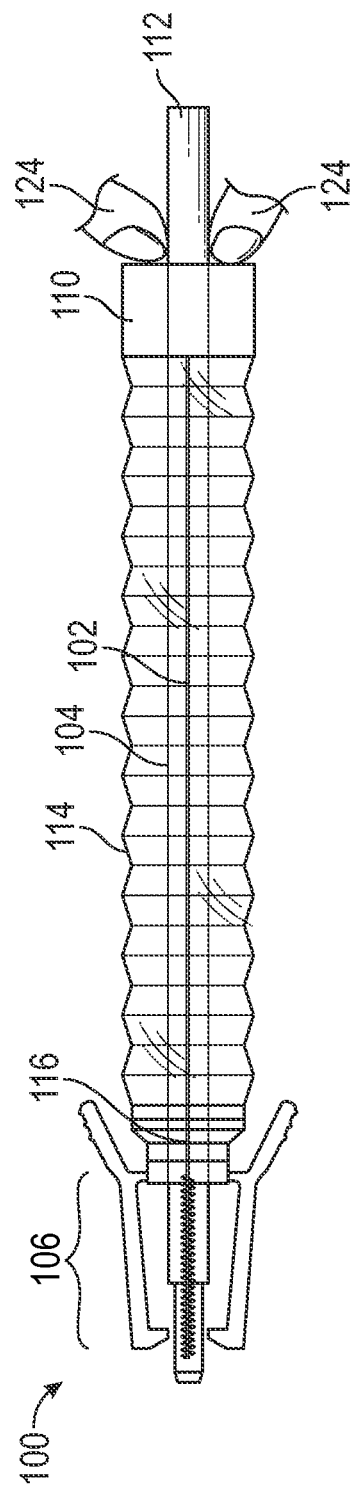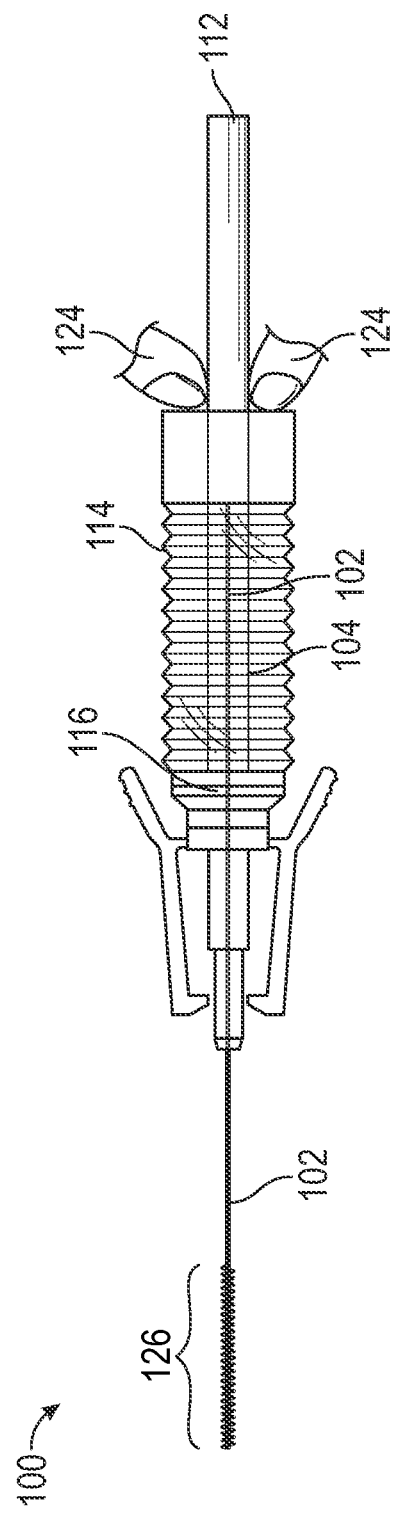
FIG. 2A
FIG. 2B

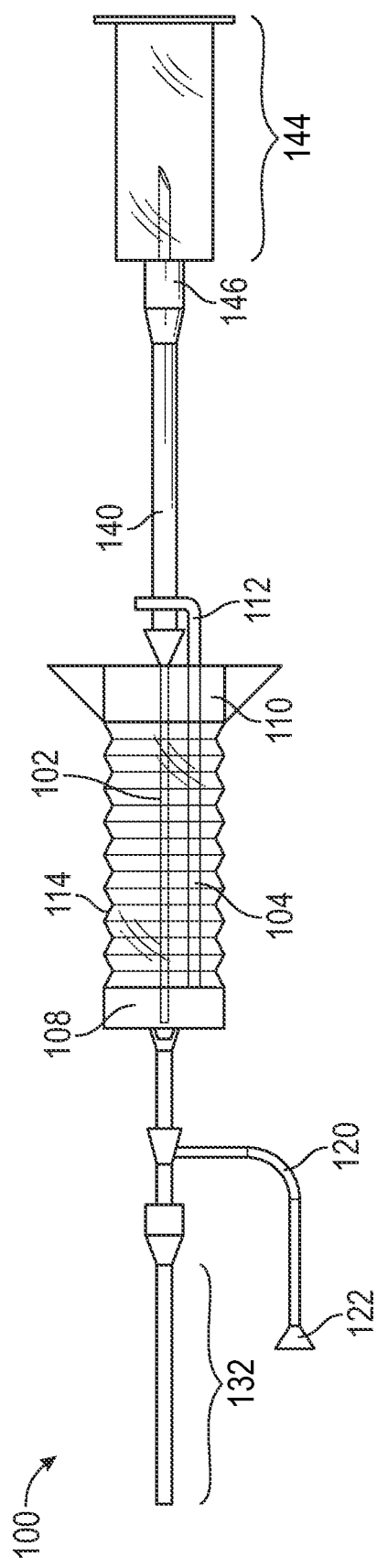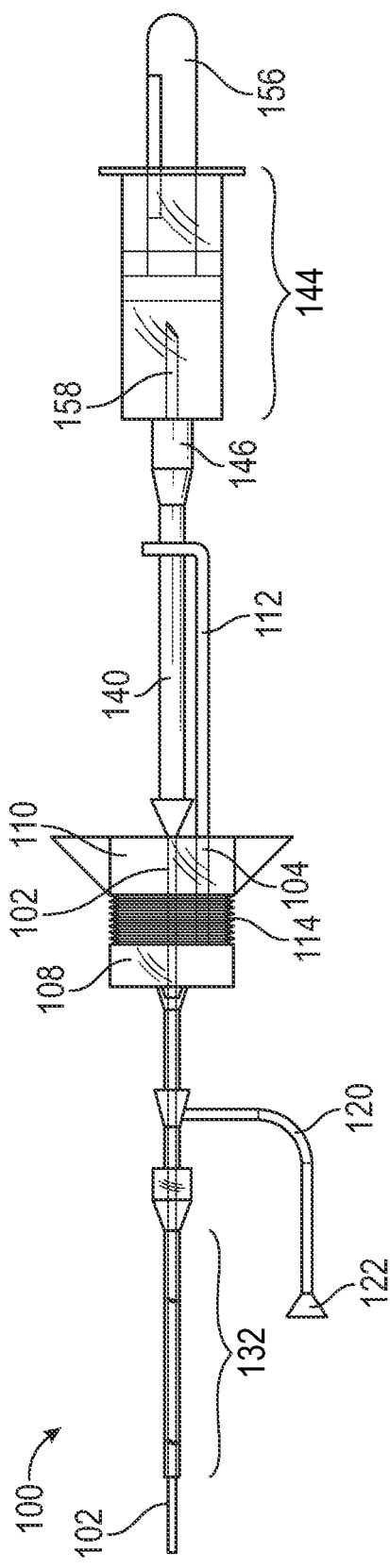
FIG. 7A
FIG. 7B

VASCULAR ACCESS DEVICE ASSEMBLY FACILITATING SINGLE-HANDED PROBE ADVANCEMENT WITH A SUPPORT MEMBER

RELATED APPLICATIONS

This application claims the benefit of U.S. Provisional Patent Application No. 62/993,680, filed on Mar. 23, 2020, entitled "VASCULAR ACCESS DEVICE ASSEMBLY FACILITATING SINGLE-HANDED PROBE ADVANCEMENT WITH A SUPPORT MEMBER," which is incorporated herein in its entirety.

BACKGROUND

Extending the patency of an intravenous (IV) device, such as a vascular access device (VAD) may improve the viability of a long-term placement and reduce the need to subject the patient to the expense and trauma of unnecessary additional intervention procedures. In further detail, during use of an IV device, the IV device is inserted into the patient's blood vessel and, in some instances, a needle is pulled out of the IV device while the IV device remains within the patient's blood vessel. In some circumstances, the IV device is left to remain in the patient's blood vessel for up to 30 days. This is done so as to allow a clinician or other health care provider (HCP) to have fluidic access to the patient's blood stream during care. This continuous fluid access to the patient's blood stream allows a clinician or other HCP to, when appropriate, draw one or more blood samples or administer one or more infusing fluids, such as a saline solution, various medicaments, and total parenteral nutrition.

The patency of the IV device may be compromised, however, while the IV device is within the patient's blood vessel. Any blockage may persist and cause the IV device to fail necessitating another administration of an IV device into the patient's body. This may increase the trauma felt by the patient and lead to other medical issues such as inflammation of the blood vessel among other medical issues.

The subject matter claimed herein is not limited to embodiments that solve any disadvantages or that operate only in environments such as those described herein. Rather, this background is provided to describe an environment in which the presently described embodiments may operate.

SUMMARY

The present disclosure relates generally to an intravenous (IV) device assembly used to interface with, for example, a vascular access device (VAD) such as a catheter assembly. In some embodiments, the IV device assembly may provide for a probe used to periodically check or improve the patency of the VAD while a needle and/or the catheter is within a patient's blood vessel. The IV device assembly may include a vascular access device (VAD) coupler at a distal end of the IV device assembly that is mechanically couplable to a VAD, the VAD coupler having a channel formed therethrough. The IV device assembly may further include, in these embodiments, a probe having a length along the IV device assembly. In these embodiments, a translation handle may be mechanically coupled to the probe so that translation of the translation handle translates the probe along the channel formed in the VAD coupler out of the distal end of the IV device assembly, and into the VAD. The IV device assembly may further include a support member formed along a length of the probe that mechanically supports the probe as it is translated within the IV device assembly. The IV device assembly may also include a fixed grip formed at a proximal end of the support member that maintains a position of a proximal end of the support member relative to the translation handle.

In these embodiments, the IV device assembly may further include a collapsible sleeve formed coaxially around the support member. In these embodiments, the collapsible sleeve may further include a coil spring 118 that creates a space around the probe and biases the translation handle towards a proximal end of the IV device assembly.

In an embodiment, the probe may be coupled to the VAD coupler, pass through a probe channel formed through the translation handle, and pass into the VAD coupler. This arrangement allows the probe to be doubled up within the IV device assembly. By doubling up on the length of the probe within the IV device assembly, the total length of the IV device assembly may be shortened or the length of the probe that extends out of the IV device assembly may be increased.

The IV device assembly may further include a support member channel into which the support member may pass and wherein the support member is keyed to fit within the support member channel and prevents the support member from rotating about a longitudinal axis of the support member.

In the embodiments described herein, the support member may take on one or more forms such as a bistable spring, a helical coil, a tube, a shell, a sleeve or combination of sleeves, among others. Each of these embodiments may provide rigidity to the IV device assembly and the probe as well during operation.

In some embodiments, the support member may include a first sleeve support member placed coaxially around the probe and a second sleeve support member placed coaxially around the probe the second sleeve support member is sized to slide coaxially within the first sleeve support member as the translation handle is translated along a length of the IV device assembly.

The present specification also describes an IV device assembly that includes a lumen forming a fluidic channel within the IV device assembly, the lumen fluidically coupled to a vascular access device (VAD) coupler connectable to a VAD and connectable to the lumen via a funnel coupler; and an IV device assembly coupler at a proximal end of the lumen; a probe having a length along the IV device assembly; a translation handle mechanically coupled to the probe that translates the probe through a VAD coupler channel formed in the VAD coupler, out of a distal end of the IV device assembly, and into the IV device assembly, the translation handle may include a lumen channel formed therethrough for the lumen to pass through as the translation handle is translated towards the distal end of the IV device assembly; a support member formed along a length of the probe that mechanically supports the probe as it is translated within the IV device assembly; and a fixed grip formed at a proximal end of the support member that maintains a position of a proximal end of the support member relative to the translation handle. A support member channel formed in the translation handle with the support member being keyed to fit within the support member channel and prevent the support member from rotating about a longitudinal axis of the support member. In an embodiment, the support member is a bistable spring that, as the translation handle is translated towards a distal end of the IV device assembly, exits the VAD coupler through a bistable spring channel and curls upon itself. In another embodiment, the support member includes a helical spring that wraps around the length of the probe.

The present specification also describes, an IV device assembly, that includes a vascular access device (VAD) coupler at a distal end of the IV device assembly that is mechanically couplable to a VAD, the VAD coupler having a channel formed therethrough; a probe having a length along the IV device assembly; a translation handle mechanically coupled to the probe via a probe spoke that, as the translation handle is translated, translates the probe through the channel, out of the distal end of the IV device assembly, and into the IV device assembly; a support member formed along a length of the probe that mechanically supports the probe as it is translated within the IV device assembly, the support member including a tube formed coaxially around the probe, the tube including a slit formed along a longitudinal length of the tube, allowing the probe spoke to pass therethrough; and a fixed grip formed at a proximal end of the support member that maintains a position of a proximal end of the support member relative to the translation handle. In this embodiment, a lumen forming a fluidic channel within the IV device assembly may be formed wherein the lumen is fluidically coupled to the VAD coupler at the distal end of the IV device assembly and an IV device assembly coupler at a proximal end of the lumen. In this embodiment, the IV device assembly may also include a collapsible sleeve formed coaxially around the probe, tube, and lumen. In some embodiments, a support spring may be formed within the collapsible sleeve that creates a space between the collapsible sleeve and the probe and biases the translation handle towards a proximal end of the IV device assembly. The IV device assembly may also include, in this embodiment, a blood sample access device fluidically and mechanically coupled to the lumen via the IV device assembly coupler. The probe in this example may be a guidewire that includes a porous distal end.

It is to be understood that both the foregoing general description and the following detailed description are exemplary and explanatory and are not restrictive of the invention, as claimed. It should be understood that the various embodiments are not limited to the arrangements and instrumentality illustrated in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 2A is a side elevation view of an IV device assembly according to some embodiments of the present disclosure;

FIG. 2B is a side elevation view of an IV device assembly according to some embodiments of the present disclosure;

FIG. 7A is a side elevation view of an IV device assembly and blood sample access device according to some embodiments of the present disclosure;

FIG. 7B is a side elevation view of an IV device assembly according to some embodiments of the present disclosure;

DESCRIPTION OF EMBODIMENTS

Figure 1:
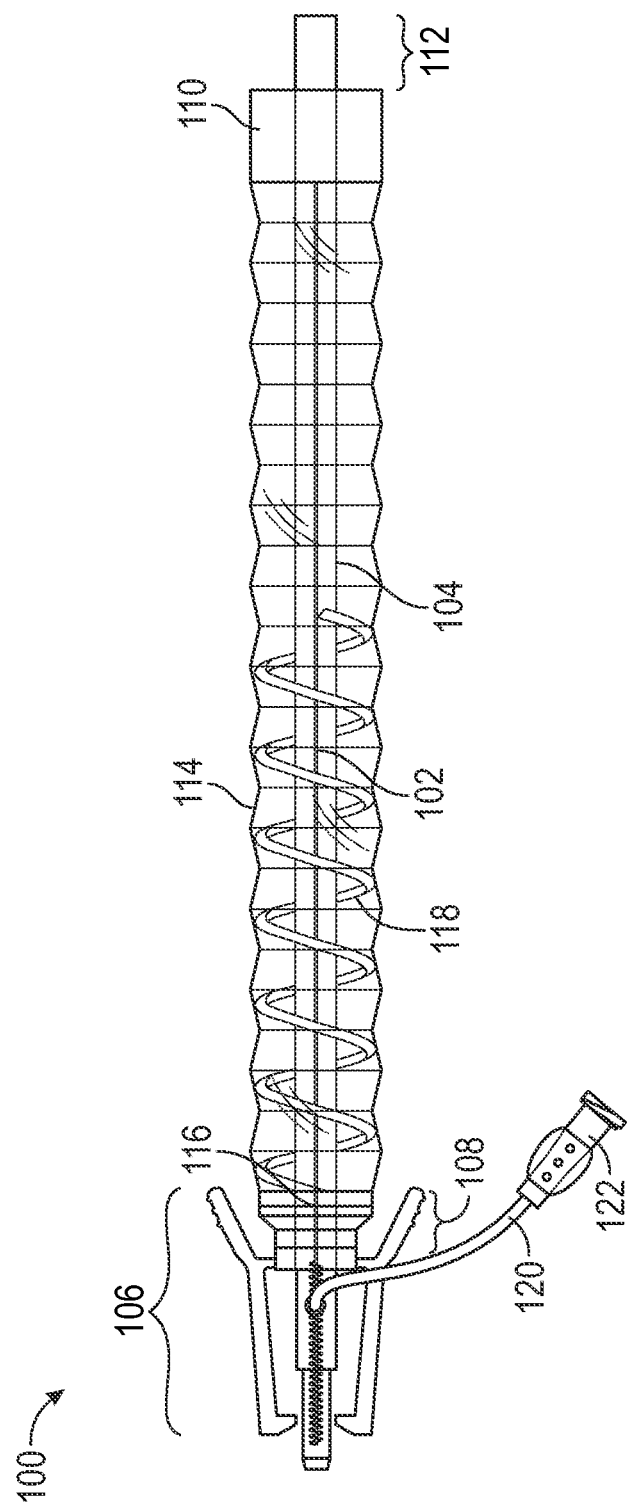
FIG. 1 is a side elevation view of an intravenous (IV) device assembly according to some embodiments of the present disclosure.

FIG. 1 is a side elevation view of an intravenous (IV) device assembly according to some embodiments of the present disclosure. In some embodiments, the IV device assembly 100 may be mechanically and fluidically coupled to a vascular access device (VAD), such as a catheter, at a VAD coupler 106. In these embodiments, the VAD may include a needle, a catheter, or a combination of a needle and catheter used to access a blood vessel of a patient. In the embodiment where the VAD includes a needle and a catheter, the needle may be removed from within the catheter once the VAD has been inserted into the patient's blood vessel. In these embodiments, the catheter may remain within the blood vessel and, as described herein may be subjected to a patency check using the probe 102 as a patency device described herein. In an embodiment, the probe 102 may include a wire, guidewire, a tube, obturator, sensor or any other device that passes through the catheter and into, at least partially, the patient's blood vessel. In some embodiments, the catheter may include a peripheral IV catheter (PIVC), a peripherally-inserted central catheter (PICC), or a midline catheter. In the embodiment where the VAD includes a needle, the probe 102 may also be used to check the patency of the needle.

In some embodiments, the IV device assembly 100 may be mechanically and fluidically coupled to a blood sample access device 144. In some embodiments, the blood sample access device 144 may be mechanically coupled to the IV device assembly coupler 146 to receive a blood sample via the IV device assembly 100, e.g., in FIG. 4. In some embodiments, the blood sample access device may include a BD VACUTAINER® LUER-LOK™ Access Device produced by Becton, Dickinson and Company of Franklin Lakes, N.J., or another suitable blood sample access device. With this blood sample access device 144, a blood sample tube such as a BD Vacutainer® produced by Becton, Dickinson and Company may be attached for use.

In an embodiment, the VAD coupler 106 may include a channel formed therethrough that, in an embodiment, allows for the probe 102 to pass into and, during operation, pass through and into a VAD as described herein. In an embodiment, the channel formed through the VAD coupler 106 may be both a mechanical channel and a fluidic channel. In this embodiment, the probe 102 may be allowed to pass through the channel formed in the VAD coupler 106 while a fluid is allowed to flow through the channel formed in the VAD coupler 106 and to a lumen formed along the length of the IV device assembly 100 and fluidically coupled to a blood sample access device described herein. In an embodiment, the channel may be formed through that VAD coupler 106 such that the channel is fluidically coupled to a port tubing 120 and port 122. The port 122 and its fluidically coupling port tubing 120 may allow for the IV device assembly 100 to be used to introduce the probe 102 into a VAD coupled to the VAD coupler 106 as well as allow for, when appropriate, drawing one or more blood samples or administer one or more infusing fluids, such as a saline solution, various medicaments, and total parenteral nutrition. As described herein, the channel formed in the VAD coupler 106 may be fluidically coupled to a lumen that runs along the length of the IV device assembly 100 and through a translation handle 110 to a fluidic reservoir or a blood sample access device.

The IV device assembly 100 further includes a support member 104. According to any embodiment described herein, the support member 104 may be any rigid, semi-rigid, or selectively rigid device that adds supportive structure to the IV device assembly 100. In an embodiment, the support member 104 may also support the probe 102 so that the probe 102 will not bend or buckle onto itself during operation of the IV device assembly 100. In the embodiment shown in FIG. 1, the support member 104 is a tube that runs along the length of the probe 102 and is formed, coaxially, around the probe 102.

As described herein, in some embodiments, the probe 102 is mechanically coupled to a translation handle 110. The translation handle 110 may be selectively moved towards a distal end or proximal end of the IV device assembly 100 so that the probe 102 is passed through and out of or into the VAD coupler 106, respectively. In an embodiment, the support member 104 may be mechanically coupled to the translation handle 110 such that a level of rigidity is provided to the IV device assembly 100 during operation.

In the embodiment shown in FIG. 1, the support member 104 passes through a support member channel formed through the translation handle 110 and may terminate at a proximal end of the support member 104 at a grip 112. The support member 104 may be used by a clinician or other health care provider (HCP) to secure a position of the IV device assembly 100 while the translation handle 110 is translated along the length of the IV device assembly 100.

In some embodiments described herein the IV device assembly 100 may include a collapsible sleeve 114. The collapsible sleeve 114 may be formed coaxially around a portion of the probe 102 and mechanically coupled to the VAD coupler 106. In some embodiments, the collapsible sleeve 114 may be made of a foldable and pliant material that allows the collapsible sleeve 114 to be collapsed in on itself. In the embodiments described herein, the collapsible sleeve 114 may be mechanically coupled to the translation handle 110. In some embodiments, the collapsible sleeve 114 may be mechanically coupled to a funnel coupler 108 that is coupled to a proximal end of the VAD coupler 106. The funnel coupler 108 may be coupled to the VAD coupler 106 via, for example, using an adhesive or by implementing an ultrasonic welding process.

As described, in some embodiments, the IV device assembly 100 may include funnel coupler 108 that is coupled to a proximal side of the VAD coupler 106. The funnel coupler 108 may include a mechanical channel formed therein to allow the probe 102 to pass therethrough. Additionally, the channel formed in the funnel coupler 108 may include a seal 116. The seal 116 may prevent any fluids present at a distal end of the seal 116 from passing out of a proximal side of the funnel coupler 108.

During operation of the IV device assembly 100, a clinician or other HCP may mechanically couple the IV device assembly 100 to a VAD via mechanically coupling the VAD coupler 106 to a coupling device of the VAD. In the example where the probe 102 is a patency device, the clinician may choose to mechanically couple the IV device assembly 100 to the VAD at a certain interval or during any other patient monitoring process. Although the present specification describes the probe 102 as a patency device, it is to be understood that any type of sensor or other device may be used as described herein to provide a number of medical diagnosis or medical treatments.

With the IV device assembly 100 mechanically coupled to the VAD at the VAD coupler 106, the clinician may grip the grip 112 with one hand and grip the translation handle 110 with the other. The clinician may then translate the translation handle 110 towards a distal end of the IV device assembly 100. Because, in the embodiment described in connection with FIG. 1, the support member 104 passes through the translation handle 110 and is mechanically coupled to the grip 112, the translation handle 110 slides along the support member 104. The support member 104 maintains a level of rigidity to the IV device assembly 100 as the translation handle 110 is translated.

Although FIG. 1 shows the support member 104 as a tube that is placed coaxially around the probe 102, the present specification contemplates that other types and forms of support members may be used. In some embodiments, the support member 104 may be a bi-stable spring, a set of telescoping sleeves, a rail, and a coiled spring. These supports members will be described herein in more detail in connection with other embodiments.

FIG. 2A is a side elevation view of an IV device assembly 100 according to some embodiments of the present disclosure. FIG. 2B is a side elevation view of an IV device assembly 100 according to some embodiments of the present disclosure. FIG. 2A shows the IV device assembly 100 with the probe 102 in a retracted state or with the probe 102 placed within the IV device assembly 100 and the translation handle 110 at a proximal end of the IV device assembly 100. FIG. 2B shows the probe 102 in a deployed state with a portion of the probe 102 extending past a distal end of the VAD coupler 106. In these embodiments, the VAD coupler 106 may be coupled to a VAD as described and, with the probe 102 in a deployed state, the probe 102 may be passed into the mechanical and/or fluidic channels formed within the VAD.

FIG. 2A shows an example position of the fingers 124 of the clinician or other HCP. In this embodiment, the clinician may place his or her fingers 124 at or around the translation handle 110 in preparation to translate the translation handle 110 towards a distal end of the IV device assembly 100 as shown in FIG. 2B. In an embodiment, the clinician may also hold onto the grip 112 so that the translation handle 110 may be moved relative to the grip 112. In an embodiment, due to the rigidity of the support member 104, the clinician may use a single hand to push against the translation handle 110 without gripping the grip 112.

FIG. 2B shows the condition of the collapsible sleeve 114 as the translation handle 110 is passed towards a distal end of the IV device assembly 100. In an embodiment, the collapsible sleeve 114 may be in the form of a bellows with one or more predefined creases within the collapsible sleeve 114 that allows the collapsible sleeve 114 to be folded onto itself as the translation handle 110 is moved distally. In an embodiment, the collapsible sleeve 114 may be pliable such that the folding of the collapsible sleeve 114 as shown in FIG. 2B is not defined by any predefined creases. In an embodiment, the collapsible sleeve 114 may include a venting port (not shown) that allows air to escape an interior volume of the collapsible sleeve 114.

The embodiments shown in FIGS. 2A and 2B do not show a funnel coupler 108 coupled to the proximal side of the VAD coupler 106. In this embodiment, the VAD coupler 106 may house the seal 116 as described herein. Again, this seal 116 may prevent any fluids from exiting a proximal side of the VAD coupler 106 when the IV device assembly 100 is mechanically coupled to a VAD that is fluidically coupled to a patient's blood vessel.

FIG. 2B also shows a porous distal end 126 formed at the end of the probe 102. In this embodiment, the probe 102 may be a patency device. The porous distal end 126 of the probe 102 may be formed to clear any fluidic channels within the VAD of any obstructions. As described herein, the patency of a VAD may be checked from time to time by a clinician. During use of a VAD, the VAD is inserted into the patient's blood vessel and, in some instances, a needle is pulled out of the VAD while the VAD remains within the patient's blood vessel. In some circumstances, the VAD is left to remain in the patient's blood vessel for up to 30 days. This is done so as to allow a clinician or other health care provider (HCP) to have fluidic access to the patient's blood stream during medical care. This continuous fluid access to the patient's blood stream allows a clinician or other HCP to, when appropriate, draw one or more blood samples or administer one or more infusing fluids, such as a saline solution, various medicaments, and total parenteral nutrition. However, the patency of the VAD may have a blockage within the fluidic channels formed therein that may persist and cause the VAD to fail necessitating another administration of a VAD into the patient's body. This may increase the trauma felt by the patient and lead to other medical issues such as inflammation of the blood vessel among other medical issues. With the used of the probe 102, the patency may be checked and maintained without removing the VAD from within the patient's body.

As described herein, the probe 102 may be another type of device that may be introduced into the patient's blood vessel in order to medically diagnose the patient or provide other types of medical care. By way of example, the probe 102 may include a thermometer formed at the distal end of the probe 102. This thermometer may be introduced into the patient's blood vessel as the translation handle 110 is translated towards a distal end of the IV device assembly 100. In another example, the probe 102 may include a pressure sensor that detects the patient's blood pressure within the patient's blood vessel. Other types of sensors also exist that may be used to measure any medical vital within the patient's blood vessel.

Although FIGS. 2A and 2B show a specific type of VAD coupler 106, the present specification contemplates that any type of coupler may be used. FIGS. 2A and 2B shows a male luer adapter as the VAD coupler 106. The present specification contemplates, however, that any other suitable VAD coupler 106 may be used including any female luer adapter as well. In some embodiments, the VAD coupler 106 may include a slip or thread female luer adapter or a slip or thread male luer adapter or any other suitable connector including a needleless connector.

Figure 3:
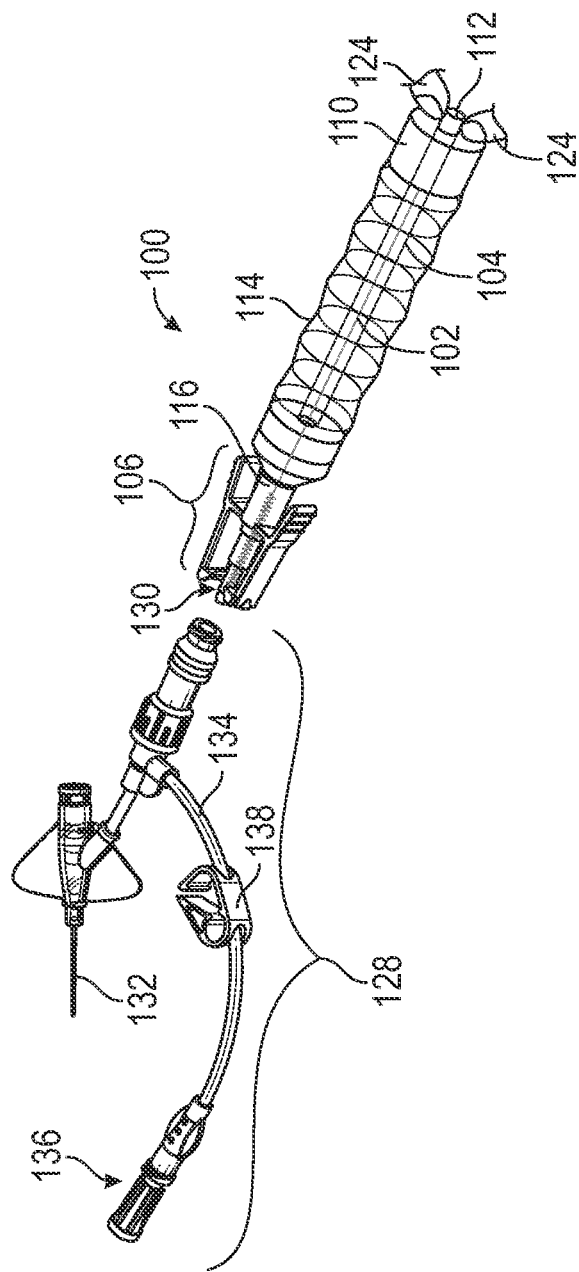
FIG. 3 is a perspective, exploded view of an IV device assembly and catheter assembly according to some embodiments of the present disclosure.

FIG. 3 is a perspective, exploded view of an IV device assembly 100 and catheter assembly 128 according to some embodiments of the present disclosure. As described herein, the IV device assembly 100 may include a VAD coupler 106 used to mechanically, and in some embodiments fluidically, couple the IV device assembly 100 to the catheter assembly 128.

In some embodiments, a catheter assembly 128 may include a catheter 132. In some embodiments, the catheter assembly 128 may include a needle and a catheter 132 formed coaxially around the needle. During operation, the needle of the catheter assembly 128 may be removed so as to leave the catheter 132 in the patient's body for fluid transfer.

In some embodiments, the catheter assembly 128 may also include a catheter port tubing 134 and catheter port 136. In some embodiments, the catheter port tubing 134 and catheter port 136 may be used as a separate access point for the clinician to introduce an infusing fluid, such as a saline solution, various medicaments, and total parenteral nutrition into the blood vessel of the patient's body. In some embodiments, in order to prevent backflow of blood into the catheter port tubing 134 and catheter port 136, the catheter port tubing 134 may include a port clamp 138. In some embodiments, the port clamp 138 may be clamped when the catheter port 136 is not in use so that pressure within the catheter port tubing 134 prevents the flow of blood therein.

Figure 4:
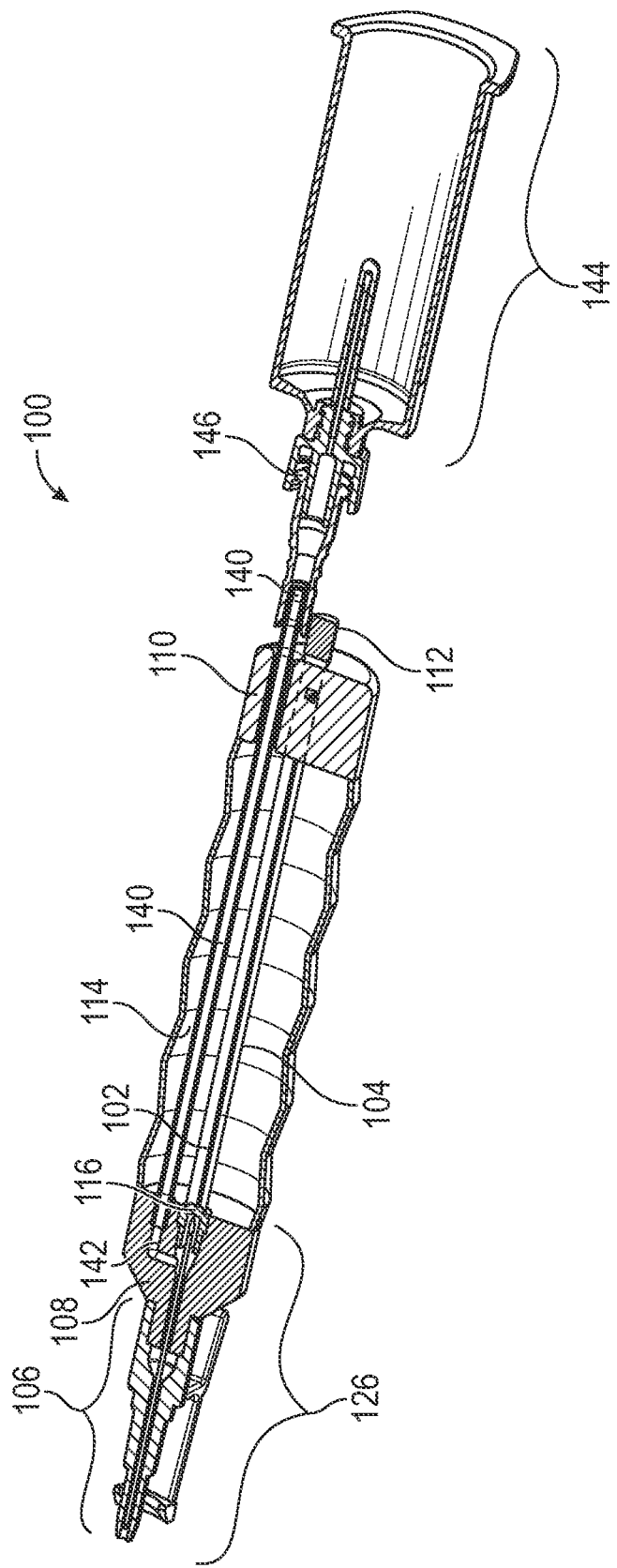
FIG. 4 is a perspective, section view of an IV device assembly and blood sample access device according to some embodiments of the present disclosure.

FIG. 4 is a perspective, section view of an IV device assembly 100 and blood sample access device 144 according to some embodiments of the present disclosure. As described herein, the IV device assembly 100 may include a VAD coupler 106 at a distal end of the IV device assembly 100. In some embodiments, the VAD coupler 106 may be mechanically coupled to a funnel coupler 108 and the VAD coupler 106 and funnel coupler 108 may have a mechanical path formed therethrough for a probe 102 to pass. In the example shown in FIG. 4, the funnel coupler 108 may also include a seal 116 that prevents any fluid that may enter the mechanical path from exiting from a proximal side of the funnel coupler 108.

In some embodiments, the IV device assembly 100 may further include a collapsible sleeve 114. As described herein, the collapsible sleeve 114 may be placed coaxially around the probe 102 so as to limit physical contact with the probe 102. By limiting physical contact with the probe 102, the collapsible sleeve 114 may limit any contaminates that may come in contact with the probe 102 that may come in fluidic contact with the patient's blood stream. In the embodiment shown in FIG. 4, the collapsible sleeve 114 may be mechanically coupled to the funnel coupler 108 and the translation handle 110 via a glue or an ultrasonic welding process. In some embodiments, the collapsible sleeve 114 may be mechanically coupled to the funnel coupler 108 and the translation handle 110 using a press fit process, a shrink fit process, or any other type of bonding process and the present specification contemplates these different types of bonding processes. In some embodiments, the air within the volume of space formed within the collapsible sleeve 114, the funnel coupler 108, and the translation handle 110 may be vented out via a vent hole (not shown) or via gaps formed between the support member 104 and a support member channel formed in the translation handle 110 as described herein.

In the embodiment shown in FIG. 4, the IV device assembly 100 may further include a lumen 140. The lumen 140 may allow for a fluid, such as blood, to be passed from a catheter assembly 128 coupled to the VAD coupler 106, through the IV device assembly 100, and into a blood sample access device 144 mechanically and fluidically coupled to the lumen 140 via an IV device assembly coupler 146. The channel formed in the VAD coupler 106 and/or the funnel coupler 108 may be both a mechanical channel for the probe 102 as well as a fluidic channel used by the lumen 140 to pass fluids therethrough.

In an embodiment, the lumen 140 may be fluidically coupled to the channel formed in the VAD coupler 106 and/or funnel coupler 108 via a funnel coupler channel 142. This allows the fluid to pass from the catheter assembly 128, into the channel formed in the VAD coupler 106, into the channel formed through the funnel coupler 108 used to house the probe 102, through the funnel coupler channel 142, into the lumen 140, and into, in this embodiment, a blood sample access device 144. In the embodiment shown in FIG. 4, therefore, the IV device assembly 100 may be used as a device to inset the probe 102 into the catheter assembly 128 (e.g., to check the patency of the catheter assembly 128) as well as a device to collect blood samples.

The blood sample access device 144, may be any type of blood sample/collection device and, in a specific embodiment, may include a BD VACUTAINER® LUER-LOK™ Access Device. In this specific example, the blood sample access device 144 may include a receptacle to receive a blood sample tube such as a BD Vacutainer®. The blood sample tube may include a septum that, when pierced by a needle formed in the blood sample access device 144, creates a negative pressure that draws blood into the blood sample tube.

In this embodiment, the lumen 140 is offset from a central axis of the IV device assembly 100 such that the funnel coupler channel 142 allows the lumen to be fluidically coupled to the channel formed in the VAD coupler 106 and/or funnel coupler 108. The probe 102 may interface with the channel formed through the VAD coupler 106 and funnel coupler 108 at, generally, the same central axis as that of the IV device assembly 100.

In some embodiments, a length of the lumen 140 may be selected based on one or more of the following: a gauge of a particular VAD, a particular VAD assembly configuration, or a clinical setup. In some embodiments, the lumen 140 may include a length L from the funnel coupler channel 142 to the IV device assembly coupler 146. In some embodiments, a fluid pathway of the lumen 140, which may be optimized, may include an inner diameter D.

Fluid flow in a fluid pathway of the lumen 140 that is tubular can be analyzed using Poiseuille's equation:

$$Q = \frac{\pi D^4 \Delta P}{128 \mu L} = \frac{\Delta P}{R_f}$$

where $\Delta P$ is a change in pressure gradient across the length of the fluid pathway, D and L are the inner diameter and length, respectively, of the fluid pathway, u is the viscosity of a fluid, and $$R_f = \frac{128\mu L}{\pi D^4}$$

is the fluid resistance. Since μ is the viscosity of the fluid and not part of the extension tube geometry, a geometric factor $G_f$ is defined such that $R_f$ (the fluid resistance) is $$R_f = \frac{128\mu}{\pi} G_f,$$

where $$G_f = \frac{L}{D^4}.$$

In some embodiments, the fluid pathway of the lumen 140 may have multiple sections with lengths (L1, L2, L3) and inner diameters of (D1, D2, D3), the geometric factor is then:

$$G_f = \frac{L1}{D1^4} + \frac{L2}{D2^4} + \frac{L3}{D3^4}$$

In some embodiments, the fluid pathway of the lumen 140 may have an inner diameter that changes over the length of the lumen 140, the geometric factor is then:

$$G_f = \int_0^L \frac{dl}{D(l)^4}$$

In some embodiments, the fluid pathway of the lumen 140 may have a cross section that is not circular or may have a complicated inner diameter profile. The geometric factor can then be determined by measuring the flow rate (Q) at given pressure (ΔP) with known viscosity (μ) fluid:

$$G_f = \frac{\pi \Delta P}{128\mu Q}$$

The $G_f$ value of the fluid pathway of the lumen 140 may be selected to reduce the maximum shear stress for each VAD gauge to be the same or less than the max shear stress of a BD 21G VACUTAINER® UltraTouch" push button blood collection set (available from Becton, Dickinson & Company of Franklin Lakes, New Jersey), which was previously considered the gold standard for blood draws. In some embodiments, the $G_f$ value of the fluid pathway may be selected to reduce the maximum shear stress for each VAD gauge to be the same or less than the max shear stress of a BD 25G VACUTAINER® UltraTouch™ push button blood collection set (available from Becton, Dickinson & Company of Franklin Lakes, New Jersey).

In some embodiments, the $G_f$ value of a fluid pathway of a lumen of the port tubing 120 may be determined similar to the $G_f$ value of the fluid pathway of the lumen 140. In some embodiments, a fluid pathway of a blood collection system, which may include the fluid pathways of one or more of the blood sample access device 144, the IV device assembly 100, and the catheter assembly 128 (which may include the catheter port tubing 134), may include an entirety of a blood collection pathway through which blood flows after leaving the blood vessel and into or through the blood sample access device 144 during blood collection. The system geometric factor $G_{fs}$ for the fluid pathway of the blood collection system can be determined in similar fashion as the $G_{fs}$ value of the fluid pathway of the lumen 140 as described earlier. In some embodiments, the system geometric factor $G_{fs}$ may be equal to or more than 7.34E+06 (1/in³). In some embodiments, $G_{fs}$ may include another value. In some embodiments, the system geometric factor $G_{fs}$ may be 7.34E+06 (1/in³) plus or minus 10 percent, plus or minus 25 percent, plus or minus 50 percent, or plus or minus 75 percent. In some embodiments, $G_{fs}$ may include another value, which may be selected based on a gauge and/or length of the catheter 132.

As described herein, the IV device assembly 100 may also include a support member 104 that provides a level of rigidity throughout the IV device assembly 100. Additionally, the support member 104 may support the probe 102 as it is moved from inside the IV device assembly 100 to extend outside of the IV device assembly 100 as described. Because the translation handle 110 is translated along the support member 104, the translation handle 110 may include a support member channel that allows the support member to pass through the translation handle 110 during operation. Similarly, because, in this embodiment, the IV device assembly 100 includes a lumen 140, the translation handle 110 may also include a lumen channel formed therethrough. The lumen channel may also allow the lumen 140 to pass through the translation handle 110 as the translation handle 110 is passed, distally, towards the VAD coupler 106 and funnel coupler 108.

As described herein, in some embodiments, the probe 102 is mechanically coupled to a translation handle 110. The translation handle 110 may be selectively moved towards a distal end or proximal end of the IV device assembly 100 so that the probe 102 is passed through and out of or into the VAD coupler 106, respectively. The probe 102, in some embodiments, may include a porous distal end 126. The porous distal end 126 of the probe 102 may be formed to clear any fluidic channels within the VAD of any obstructions. As described herein, the patency of a VAD may be checked from time to time by a clinician. During use of a VAD, the VAD is inserted into the patient's blood vessel and, in some instances, a needle is pulled out of the VAD while the VAD remains within the patient's blood vessel. In some circumstances, the VAD is left to remain in the patient's blood vessel for up to 30 days. This is done so as to allow a clinician or other health care provider (HCP) to have fluidic access to the patient's blood stream during medical care.

Figure 5:
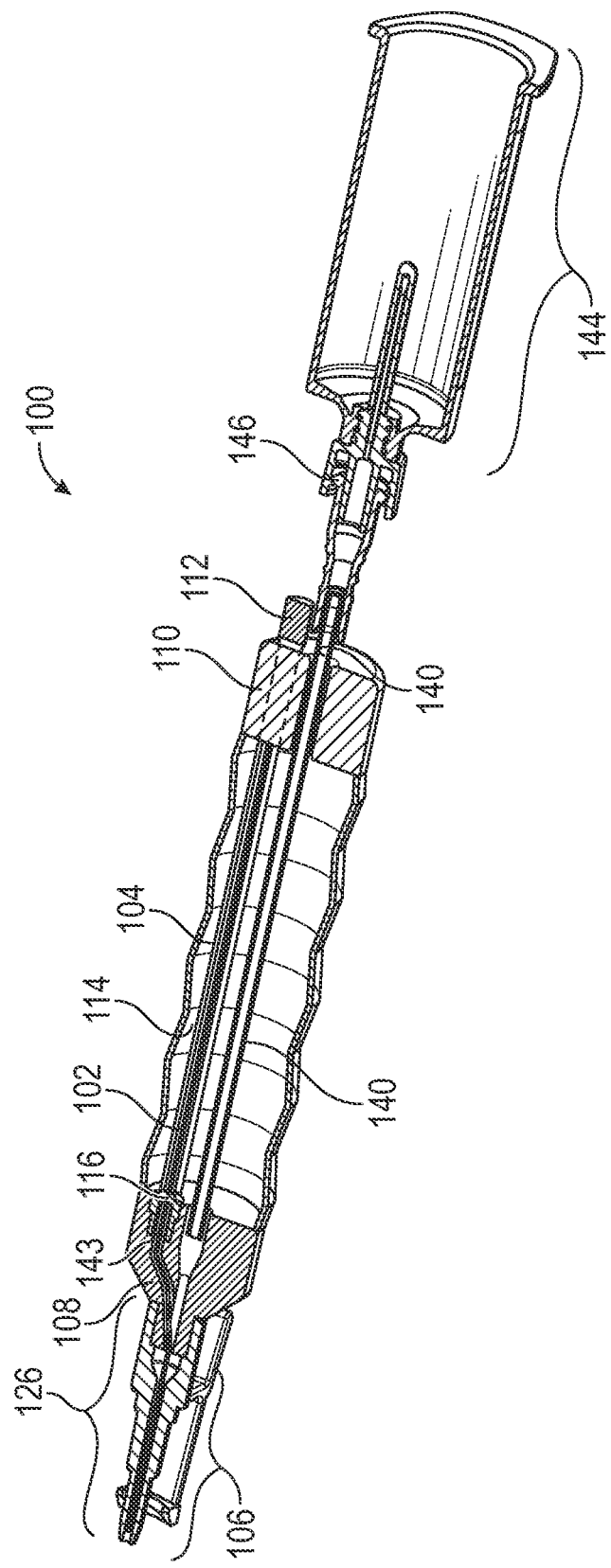
FIG. 5 is a perspective, section view of an IV device assembly and blood sample access device according to some embodiments of the present disclosure.

FIG. 5 is a perspective, section view of an IV device assembly 100 and blood sample access device according to some embodiments of the present disclosure. As described herein, the IV device assembly 100 may include a VAD coupler 106 at a distal end of the IV device assembly 100. In some embodiments, the VAD coupler 106 may be mechanically coupled to a funnel coupler 108 and the VAD coupler 106 and funnel coupler 108 may have a mechanical path formed therethrough for a probe 102 to pass. In the example shown in FIG. 4, the funnel coupler 108 may also include a seal 116 that prevents any fluid that may enter the mechanical path from exiting from a proximal side of the funnel coupler 108.

In some embodiments, the IV device assembly 100 may further include a collapsible sleeve 114. As described herein, the collapsible sleeve 114 may be placed coaxially around the probe 102 so as to limit physical contact with the probe 102. By limiting physical contact with the probe 102, the collapsible sleeve 114 may limit any contaminates that may come in contact with the probe 102 that may come in fluidic contact with the patient's blood stream. In the embodiment shown in FIG. 4, the collapsible sleeve 114 may be mechanically coupled to the funnel coupler 108 and the translation handle 110 via a glue or an ultrasonic welding process. In some embodiments, the air within the volume of space formed within the collapsible sleeve 114, the funnel coupler 108, and the translation handle 110 may be vented out via a vent hole (not shown) or via gaps formed between the support member 104 and a support member channel formed in the translation handle 110 as described herein.

In the embodiment shown in FIG. 5, the IV device assembly 100 may further include a lumen 140. The lumen 140 may allow for a fluid, such as blood, to be passed from a catheter assembly 128 coupled to the VAD coupler 106, through the IV device assembly 100, and into a blood sample access device 144 mechanically and fluidically coupled to the lumen 140 via an IV device assembly coupler 146. The channel formed in the VAD coupler 106 and/or the funnel coupler 108 may be both a mechanical channel for the probe 102 as well as a fluidic channel used by the lumen 140 to pass fluids therethrough.

FIG. 5 shows that, in some embodiments, the positions of the lumen 140 and the probe 102 and support member 104 may been swapped as compared to FIG. 4. Specifically, the probe 102 is offset from a central axis of the IV device assembly 100 such that the probe 102 passes through a probe channel 143 that allows the probe 102 to be passed to the channel formed in the VAD coupler 106 and/or funnel coupler 108. The probe 102 may be made of an elastically pliable material that allows the probe 102 to pass through the probe channel 143 and into the channel formed in the VAD coupler 106 during operation of the IV device assembly 100. In this embodiment, the lumen 140 may interface with the channel formed through the VAD coupler 106 and funnel coupler 108 at, generally, the same central axis as that of the IV device assembly 100.

As described herein, the IV device assembly 100 may also include a support member 104 that provides a level of rigidity throughout the IV device assembly 100. Additionally, the support member 104 may support the probe 102 as it is moved from inside the IV device assembly 100 to extend outside of the IV device assembly 100 as described. Because the translation handle 110 is translated along the support member 104, the translation handle 110 may include a support member channel that allows the support member to pass through the translation handle 110 during operation. Similarly, because, in this embodiment, the IV device assembly 100 includes a lumen 140, the translation handle 110 may also include a lumen channel formed therethrough. The lumen channel may also allow the lumen 140 to pass through the translation handle 110 as the translation handle 110 is passed, distally, towards the VAD coupler 106 and funnel coupler 108.

As described herein, in some embodiments, the probe 102 is mechanically coupled to a translation handle 110. The translation handle 110 may be selectively moved towards a distal end or proximal end of the IV device assembly 100 so that the probe 102 is passed through and out of or into the VAD coupler 106, respectively. The probe 102, in some embodiments, may include a porous distal end 126. The porous distal end 126 of the probe 102 may be formed to clear any fluidic channels within the VAD of any obstructions. As described herein, the patency of a VAD may be checked from time to time by a clinician. During use of a VAD, the VAD is inserted into the patient's blood vessel and, in some instances, a needle is pulled out of the VAD while the VAD remains within the patient's blood vessel. In some circumstances, the VAD is left to remain in the patient's blood vessel for up to 30 days. This is done so as to allow a clinician or other health care provider (HCP) to have fluidic access to the patient's blood stream during medical care.

Figure 6A:
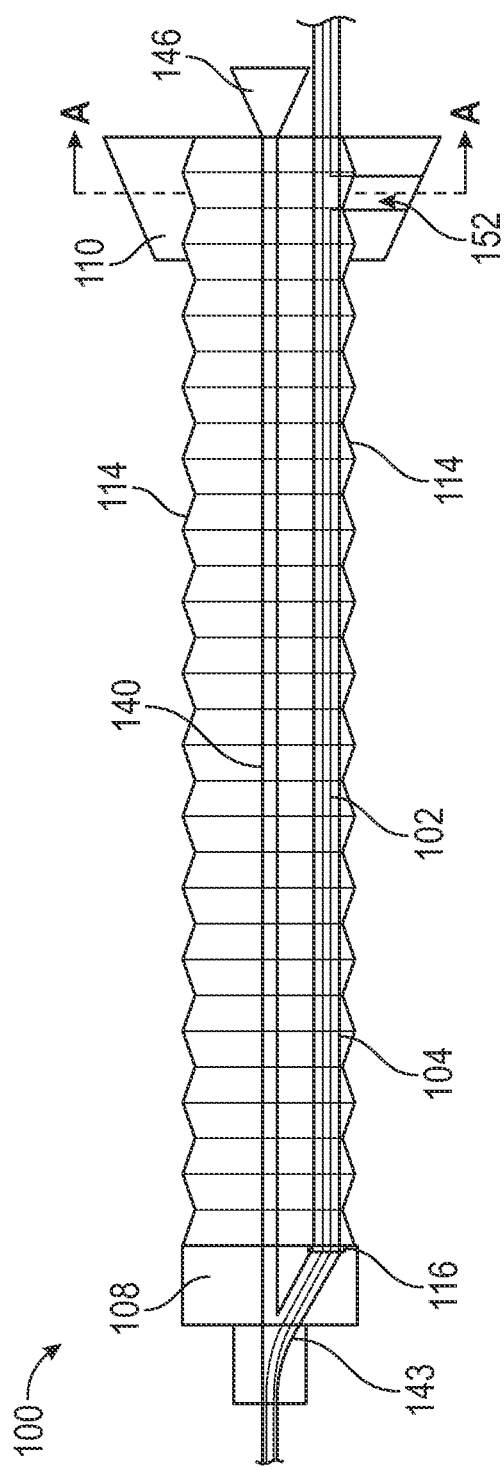
FIG. 6A is a side elevation view of an IV device assembly according to some embodiments of the present disclosure.
Figure 6C:
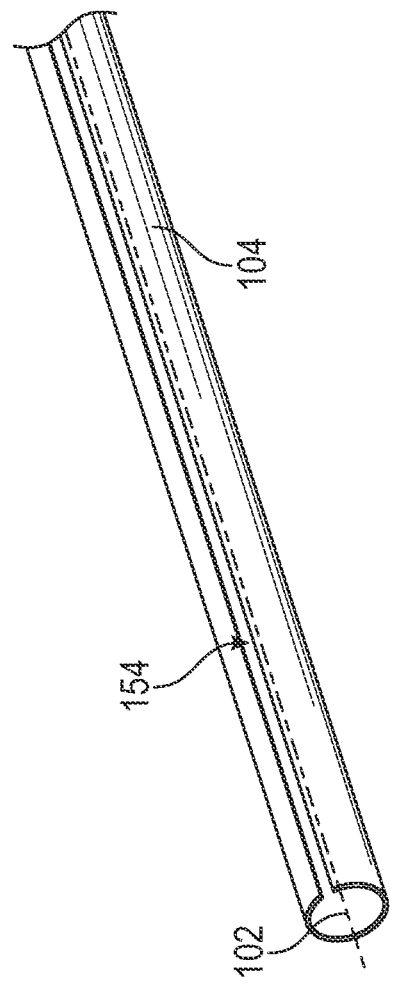
FIG. 6C is a perspective view of a support member of the IV device assembly according to some embodiments of the present disclosure.
Figure 6B:
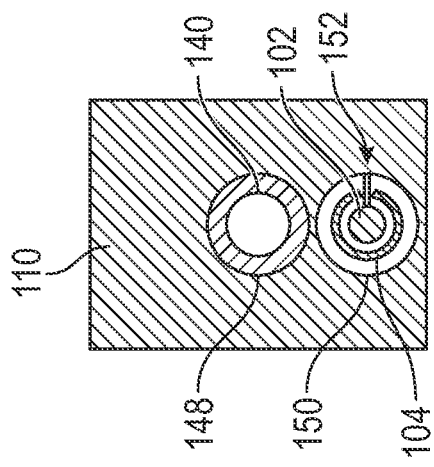
FIG. 6B is a front elevation, section view of a translation handle of the IV device assembly according to some embodiments of the present disclosure.

FIG. 6A is a side elevation view of an IV device assembly 100 according to some embodiments of the present disclosure. FIG. 6B is a front elevation, section view (e.g., along section "A" shown in FIG. 6A) of a translation handle 110 of the IV device assembly 100 according to some embodiments of the present disclosure. FIG. 6C is a perspective view of a support member 104 of the IV device assembly 100 according to some embodiments of the present disclosure. In the embodiments shown in FIGS. 6A and 6B, the probe 102 is shown to be in an offset position relative to a central, longitudinal axis of the IV device assembly 100 and similar to that shown in FIG. 4.

In the embodiments shown in FIGS. 6A, 6B, and 6C, the IV device assembly 100 may include a VAD coupler (not shown) at a distal end of the IV device assembly 100. In some embodiments, the VAD coupler may be mechanically coupled to a funnel coupler (not shown) and the VAD coupler and funnel coupler may have a mechanical path formed therethrough for a probe 102 to pass. In an example, the IV device assembly 100 may also include a seal 116 that prevents any fluid that may enter the mechanical path from exiting from a proximal side of the VAD coupler or funnel coupler.

In some embodiments, the IV device assembly 100 may further include a collapsible sleeve 114. As described herein, the collapsible sleeve 114 may be placed coaxially around the probe 102 so as to limit physical contact with the probe 102. By limiting physical contact with the probe 102, the collapsible sleeve 114 may limit any contaminates that may come in contact with the probe 102 that may come in fluidic contact with the patient's blood stream. In the embodiment shown in FIG. 4, the collapsible sleeve 114 may be mechanically coupled to the funnel coupler 108 and the translation handle 110 via a glue or an ultrasonic welding process. In some embodiments, the air within the volume of space formed within the collapsible sleeve 114, the funnel coupler 108, and the translation handle 110 may be vented out via a vent hole (not shown) or via gaps formed between the support member 104 and a support member channel formed in the translation handle 110 as described herein. In an embodiment, the funnel coupler 108 and/or VAD coupler, may include a probe channel 143. The probe channel 143 may be formed into one or both of the VAD coupler or funnel coupler 108 so that the probe 102 may be passed into and out of the IV device assembly 100 during operation.

As described herein, the translation handle 110 may include a lumen channel 148 and a support member channel 150. The lumen channel 148 may be formed through the translation handle 110 so that the translation handle 110 may translate towards the distal end of the IV device assembly 100 while allowing the lumen 140 to remain connected to, for example, a IV device assembly coupler 146 and a blood sample access device (not shown).

The support member channel 150 may also allow for a channel through which the support member 104 may be passed as the translation handle 110 is translated towards a distal end of the IV device assembly 100. In order to move the probe 102 with the translation handle 110, however, the translation handle 110 may also include a spoke 152. The spoke 152 may, in example, be an extension of the translation handle 110 that passes radially into the support member channel 150 and is mechanically coupled to the probe 102. In another embodiment, the spoke 152 may be a single mechanical coupling device that couples to the translation handle 110, extends into the support member channel 150, and coupled to the probe 102 at a proximal or near-proximal location along the probe 102.

In the embodiments, shown in FIGS. 6A, 6B, and 6C, the IV device assembly 100 includes a support member 104 in the shape of a tube that extends down a length of the IV device assembly 100. In an embodiment, the support member 104 may be as long or longer than the distance that the collapsible sleeve 114 and translation handle 110 can extend thereby allowing the support member 104 to extend past the proximal side of the translation handle 110. In this embodiment, the support member 104 may include a grip (not shown) for the clinician to grasp while the clinician is translating the translation handle 110 towards the distal end of the IV device assembly 100.

In an embodiment, the support member 104 may be in the form of a tube as shown in FIG. 6C. The probe 102 is placed coaxially within the tube-shaped support member 104. In this embodiment, the tubular-shaped support member 104 may include a slit 154 down the length of the support member 104 so that the spoke 152 may be translated through the support member 104. In an embodiment, the tube-shaped support member 104 may be made of a pliable material such as a plastic that is allowed to elastically bend wherever the spoke 152 enters the support member 104 at any location along the slit 154 made in the support member 104. During translation of the translation handle 110, therefore, the spoke 152 may bend open the support member 104 at the location of the slit 154 where the spoke 152 couples the probe 102 to the translation handle 110.

Figure 7C:
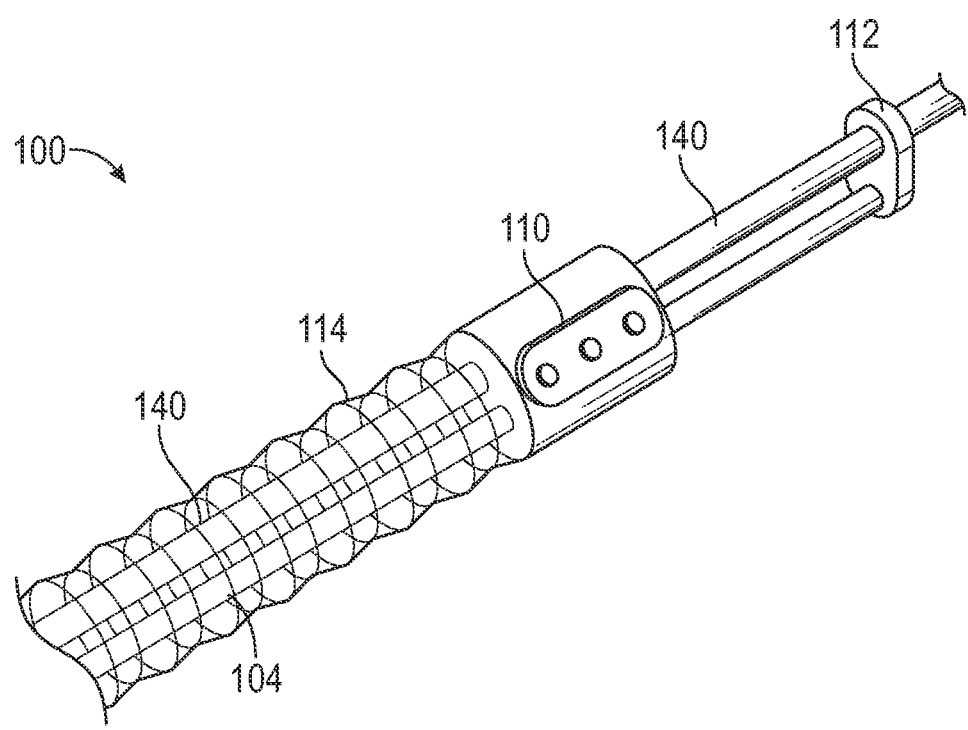
FIG. 7C is a perspective view of an IV device assembly and blood sample access device according to some embodiments of the present disclosure.

FIG. 7A is a side elevation view of an IV device assembly 100 and blood sample access device 144 according to some embodiments of the present disclosure. FIG. 7B is a side elevation view of an IV device assembly according to some embodiments of the present disclosure. FIG. 7C is a perspective view of an IV device assembly and blood sample access device according to some embodiments of the present disclosure. In the embodiment shown in FIGS. 7A and 7B, the IV device assembly 100 may include a needle/catheter distal end 130 directly, fluidically and mechanically coupled to a distal side of the funnel coupler 108. Although, the present specification also contemplates the VAD coupler (not shown) may also be used as described in connection with FIG. 1. In the embodiment shown in FIGS. 7A and 7B, the IV device assembly 100 may include a probe 102 and a lumen 140 that is mechanically and fluidically coupled to the needle/catheter distal end 130, respectively. The interface between the probe 102 and the support member 104 has been described herein using a plurality of embodiments. In these embodiments, the lumen 140 may be placed alongside the probe 102 such that the point where the probe 102 and lumen 140 enter the funnel coupler 108 are relatively close together. This allows little deflection of the probe 102 as it enters the fluid path of the lumen 140 within the funnel coupler 108. In these embodiments, either a funnel coupler channel 142 or a probe channel 143 may be used as described to allow for the two paths of the probe 102 and lumen 140 to converge within the funnel coupler 108. Still further, a seal (not shown) may be used to seal the entrance point of the/102 into the funnel coupler 108 from fluid thereby preventing fluids from leaking out of a proximal side of the funnel coupler 108.

The support member 104 described herein may provide a rigidity of the IV device assembly 100. In this specific embodiment, a distal end of the support member 104 is mechanically coupled to a proximal side of the funnel coupler 108. In an alternative embodiment, the support member 104 and the funnel coupler 108 may be formed of a single monolithic piece. In either embodiment, the support member 104 may be passed through the translation handle 110 and be made to couple coaxially around the lumen 140. The support member 104 may, in an embodiment, include a ring at its distal end that allows for, during manufacture, the lumen 140 to be passed therethrough. Because the lumen 140 may be made of a pliable material such as plastic, the support member may support the lumen 140 as well as the other elements of the IV device assembly 100 during operation. In an embodiment, this ring of the support member 104 formed around the lumen 140 may serve as a grip 112 as described herein.

During operation, a clinician or other HCP may fluidically couple the blood sample access device 144 to a proximal end of the lumen 140 in preparation to receive a blood sample. Either prior to or after receiving the blood sample, the clinician may check or maintain the patency of the needle/catheter distal end 130 by translating the translation handle 110 towards a distal end of the IV device assembly 100. The clinician may grip the translation handle 110 and, for example, the blood sample access device 144 and translate the translation handle 110 along the support member 104 and lumen 140 thereby allowing the support member 104 and lumen 140 to pass through a support member channel 150 and a lumen channel 148 formed within the translation handle 110, respectively. As the distal translation of the IV device assembly 100 occurs, the collapsible sleeve 114 may be folded in onto itself. The distal translation of the translation handle 110 may end, in an embodiment, with a distal side of the translation handle 110 touching a proximal side of the funnel coupler 108. This translation causes the probe 102 to extend out of the needle/catheter distal end 130 as shown in FIG. 7B and past a distal end of the needle/catheter distal end 130. Where the probe 102 is a patency device, the fluidic channels within the needle/catheter distal end 130 and funnel coupler 108 have been checked and patency restored where it once may not have existed. Where the probe 102 is, for example, a thermometer, the temperature of the patient may be taken and noted by the clinician. Other types of probes 102 may exist as described herein, and the present specification contemplates the use of these other types of probe 102.

After patency checking, in this embodiment, the clinician may retrieve a blood sample by inserting a blood sample tube 156 into the blood sample access device 144 as depicted in FIG. 7B. In an embodiment, the blood sample access device 144 may be a BD VACUTAINER® LUER-LOK™ and the blood sample tube 156 may be a BD Vacutainer®. In this specific example, as the blood sample tube 156 is inserted into the blood sample access device 144, a access device needle 158 may be allowed to pierce a septum formed at a distal end of the blood sample tube 156 causing a negative pressure formed within the blood sample tube 156 to be released and draw an amount of blood into the blood sample tube 156 via the lumen 140. When a sufficient amount of blood is retrieved, the clinician may remove the blood sample tube 156 causing the septum to be sealed up. This blood retrieval process may be conducted any number of times during the indwelling of the needle/catheter distal end 130 and the probe 102, when used as a patency device, may be implemented to maintain the patency of the needle/catheter distal end 130.

In this embodiment, the IV device assembly 100 may also include a fluidically coupling port tubing 120 and a port 122. As described herein, the fluidically coupling port tubing 120 and port 122 may be used to administer one or more infusing fluids, such as a saline solution, various medicaments, and total parenteral nutrition when appropriate during the medical care of the patient.

Figure 8A:
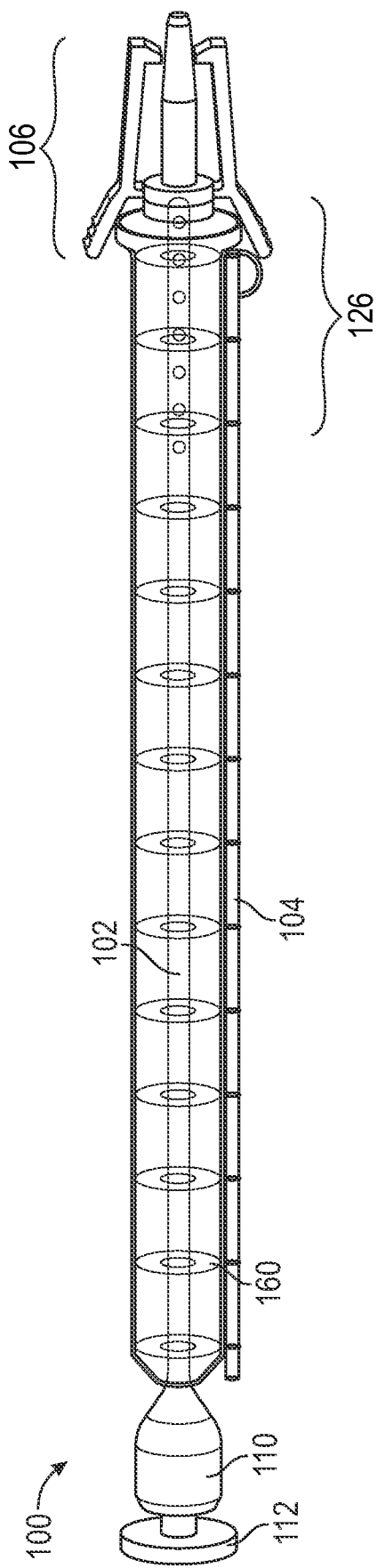
FIG. 8A is a perspective view of an IV device assembly according to some embodiments of the present disclosure.
Figure 8B:
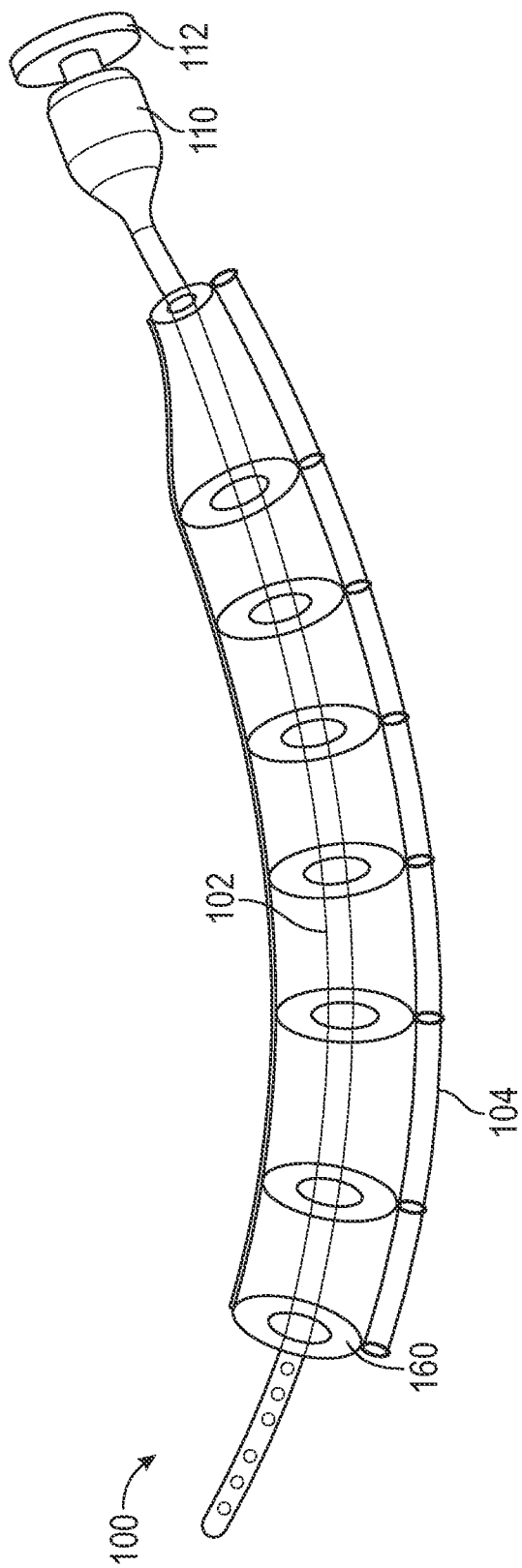
FIG. 8B is a perspective view of an IV device assembly according to some embodiments of the present disclosure.

FIG. 8A is a perspective view of an IV device assembly 100 according to some embodiments of the present disclosure. FIG. 8B is a perspective view of an IV device assembly 100 according to some embodiments of the present disclosure. In these embodiments, the IV device assembly 100 may include a VAD coupler 106 at a distal end and a translation handle 110 and grip 112 formed at a proximal end as described herein.

In this embodiment, the support member 104 may include a plurality of rings 160 placed coaxially around the probe 102 and secured to each other using a rod or spine that is mechanically coupled to each ring 160. In the embodiment shown in FIG. 8A, the rod or spine may be made straight. In this embodiment, each ring 160 may support the collapsible sleeve 114 as the translation handle 110 is translated distally. Each ring 160 may also be slidably coupled to the rod or spine such that each ring 160 may be translated along the length of the rod or spine.

In the embodiment shown in FIG. 8B, the rod or spine of the support member 104 may be bent. The bent rod or spine may provide greater support to the IV device assembly 100 during use. Again, each ring 160 may support the collapsible sleeve 114 as the translation handle 110 is translated distally. Each ring 160 may also be slidably coupled to the rod or spine such that each ring 160 may be translated along the length of the rod or spine.

Figure 9A:
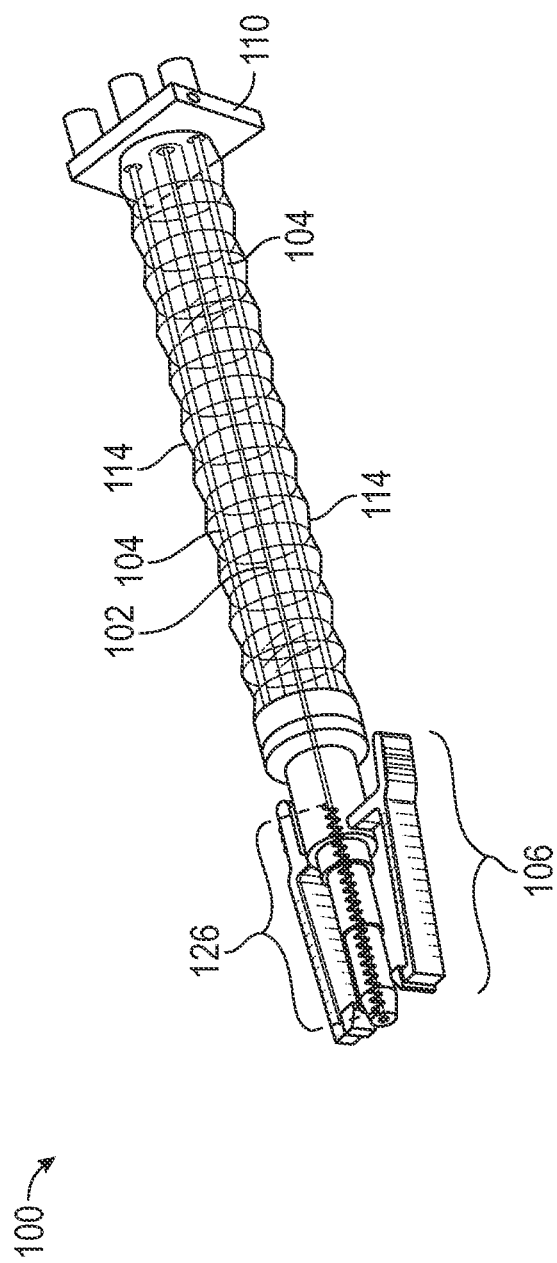
FIG. 9A is a perspective view of an IV device assembly according to some embodiments of the present disclosure.
Figure 9B:
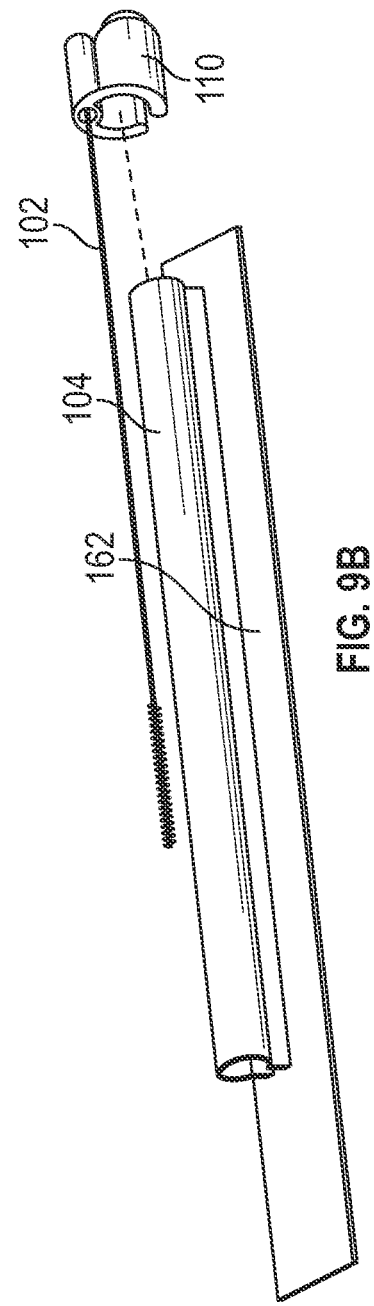
FIG. 9B is a perspective view of a translation handle and support member of an IV device assembly according to some embodiments of the present disclosure.

FIG. 9A is a perspective view of an IV device assembly 100 according to some embodiments of the present disclosure. FIG. 9B is a perspective view of a translation handle 110 and support member 104 of an IV device assembly 100 according to some embodiments of the present disclosure. In this embodiment, the IV device assembly 100 may include a VAD coupler 106 placed at a distal end of the IV device assembly 100. Other elements related to the IV device assembly 100 and shown and described in connection with other embodiments described herein may also be included with the IV device assembly 100 shown in FIGS. 9A and 9B.

FIG. 9A shows that the support member may include a rail mechanically coupled to an internal support structure 162. In this embodiment, the rails may be mechanically coupled to the translation handle 110 such that the translation handle 110 is allowed to pass along the rails. As shown in FIG. 6B, a portion of the translation handle 110 may be mechanically coupled to a proximal end of the probe 102 that may be wrapped, partially, around the rail when assembled. The support member 104 may, in this embodiment, structurally support the IV device assembly 100 as a whole while also preventing the probe 102 from bending as force is applied to the proximal end of the probe 102.

The probe 102, in some embodiments, may include a porous distal end 126. The porous distal end 126 of the probe 102 may be formed to clear any fluidic channels within the VAD of any obstructions. As described herein, the patency of a VAD may be checked from time to time by a clinician. During use of a VAD, the VAD is inserted into the patient's blood vessel and, in some instances, a needle is pulled out of the VAD while the VAD remains within the patient's blood vessel. In some circumstances, the VAD is left to remain in the patient's blood vessel for up to 30 days. This is done so as to allow a clinician or other HCP to have fluidic access to the patient's blood stream during medical care.

Figure 10A:
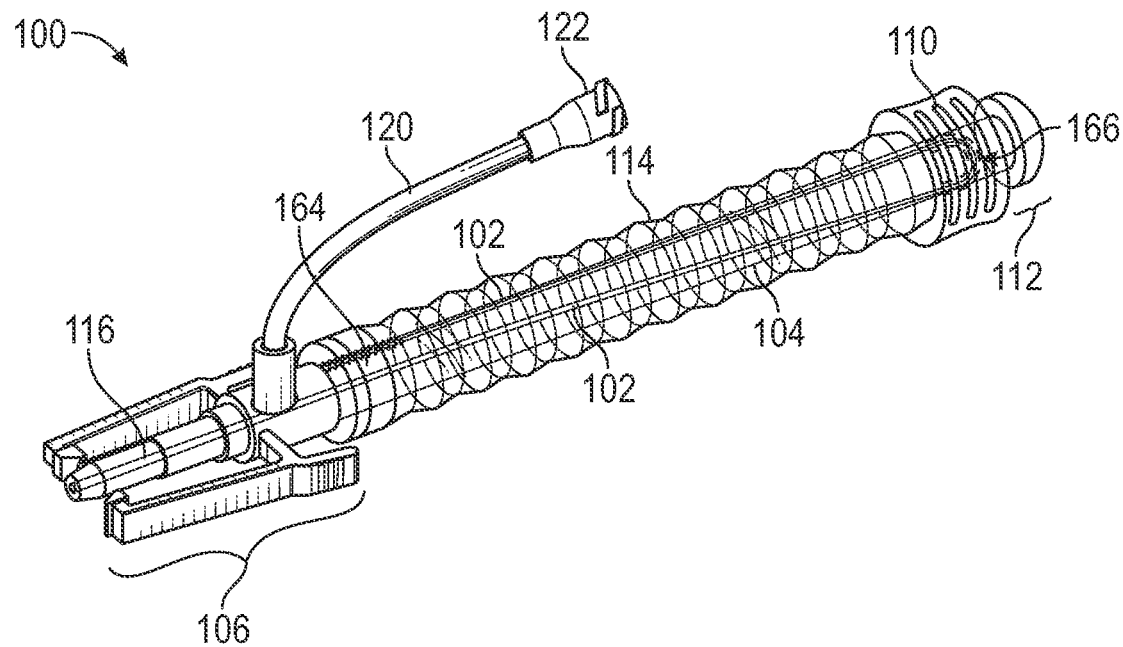
FIG. 10A is perspective view of an IV device assembly according to some embodiments of the present disclosure.
Figure 10B:
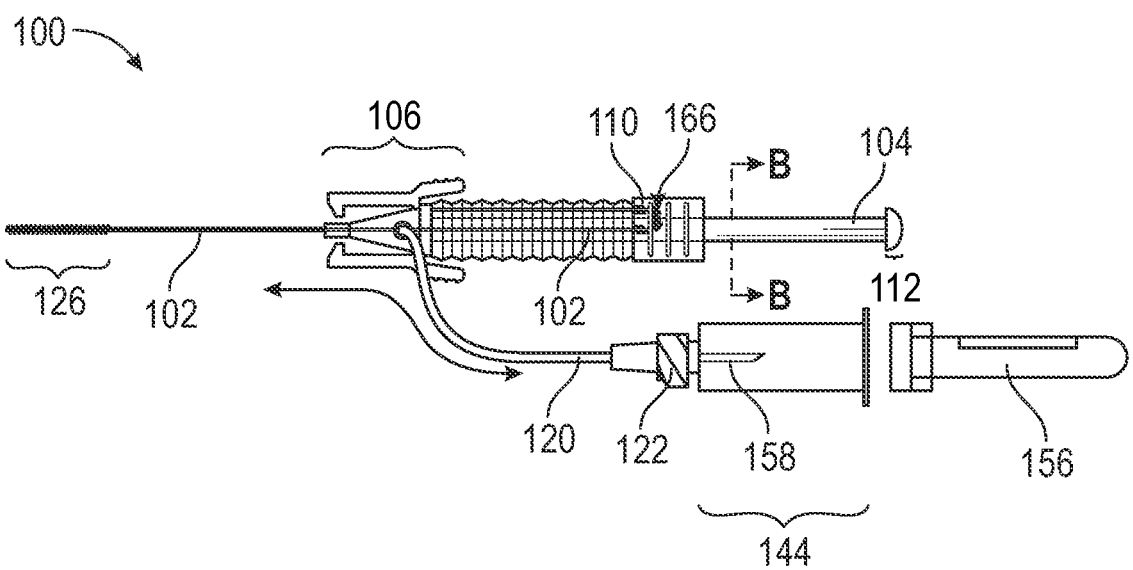
FIG. 10B is a side elevation view of an IV device assembly according to some embodiments of the present disclosure.

FIG. 10A is perspective view of an IV device assembly 100 according to some embodiments of the present disclosure. FIG. 10B is a side elevation view of an IV device assembly 100 according to some embodiments of the present disclosure. In some embodiments, the IV device assembly 100 may be mechanically and fluidically coupled to a vascular access device (VAD), such as a catheter, at a VAD coupler 106. In these embodiments, the VAD may include a needle, a catheter, or a combination of a needle and catheter used to access a blood vessel of a patient. In the embodiment where the VAD includes a needle and a catheter, the needle may be removed from within the catheter once the VAD has been inserted into the patient's blood vessel. In these embodiments, the catheter may remain within the blood vessel and, as described herein may be subjected to a patency check using the probe 102 as a patency device described herein. In an embodiment, the probe 102 may include a wire, guidewire, a tube, obturator, sensor or any other device that passes through the catheter and into, at least partially, the patient's blood vessel. In some embodiments, the catheter may include a peripheral IV catheter (PIVC), a peripherally-inserted central catheter (PICC), or a midline catheter. In the embodiment where the VAD includes a needle, the probe 102 may also be used to check the patency of the needle.

In some embodiments, the IV device assembly 100 may be mechanically and fluidically coupled to a blood sample access device (not shown). In some embodiments, the blood sample access device may be mechanically coupled to the IV device assembly coupler (not shown) to receive a blood sample via the IV device assembly 100. In some embodiments, the blood sample access device may include a BD VACUTAINER® LUER-LOK™ Access Device produced by Becton, Dickinson and Company of Franklin Lakes, New Jersey, or another suitable blood sample access device. With this blood sample access device, a blood sample tube such as a BD Vacutainer® produced by Becton, Dickinson and Company.

In an embodiment, the VAD coupler 106 may include a channel formed therethrough that, in an embodiment, allows for the probe 102 to pass into and, during operation, pass through and into a VAD as described herein. In an embodiment, the channel formed through the VAD coupler 106 may be both a mechanical channel and a fluidic channel. In this embodiment, the probe 102 may be allowed to pass through the channel formed in the VAD coupler 106 while a fluid is allowed to flow through the channel formed in the VAD coupler 106 and to a lumen formed along the length of the IV device assembly 100 and fluidically coupled to a blood sample access device described herein.

In an embodiment, the channel formed through that VAD coupler 106 such that the channel is fluidically coupled to a port tubing 120 and port 122. The port 122 and its fluidically coupling port tubing 120 and may allow for the IV device assembly 100 to be used to introduce the probe 102 into a VAD coupled to the VAD coupler 106 as well as allow for, when appropriate, draw one or more blood samples or administer one or more infusing fluids, such as a saline solution, various medicaments, and total parenteral nutrition. In an embodiment, the channel formed in the VAD coupler 106 may be fluidically coupled to a lumen the runs along the length of the IV device assembly 100 and through a translation handle 110 to a fluidic reservoir or a blood sample access device. In some embodiments, the lumen may correspond to the lumen 140 (see, for example, FIG. 4). In an embodiment, the port 122 may be mechanically and fluidically coupled to a blood sample access device 144 so that a blood sample at a blood sample tube 156 may be received. In this embodiment, the port 122 may be selectively coupled to one of a blood sample access device or a medicament introduction device.

The IV device assembly 100 further includes a support member 104. According to any embodiment described herein, the support member 104 may be any rigid, semi-rigid, or selectively rigid device that adds supportive structure to the IV device assembly 100. In an embodiment, the support member 104 may also support the probe 102 so that the probe 102 will not bend or buckle onto itself during operation of the IV device assembly 100. In the embodiment shown in FIGS. 10A and 10B, the support member 104 is rigid shaft that runs along the length of the probe 102 and is passed through a support member channel formed in the translation handle 110.

As described herein, in some embodiments, the probe 102 is mechanically coupled to a translation handle 110. The translation handle 110 may be selectively moved towards a distal end or proximal end of the IV device assembly 100 so that the probe 102 is passed through and out of or into the VAD coupler 106, respectively. In an embodiment, the support member 104 may be mechanically coupled to the translation handle 110 such that a level of rigidity to the IV device assembly 100 during operation. In the specific embodiment shown in FIGS. 10A and 10B, the probe 102 is a double-length probe 102. The doubling of the length of the probe 102 may be accomplished by mechanically coupling a proximal end of the probe 102 to an anchor 164 point formed on a proximal side of the VAD coupler 106, or in some embodiments, a proximal side of the funnel coupler. In this embodiment, the probe 102 may be passed through a channel 166 formed in the translation handle 110 and directed through the IV device assembly 100 to the channel formed through the VAD coupler 106 and/or funnel coupler. During operation, as the IV device assembly 100 is translated distally, the probe 102 is forced through the channel 166 and out of the VAD coupler 106. In some embodiments, the grip 112 may be pinched in between a thumb and a finger 124 of a first hand of the clinician. In these and other embodiments, another finger 124, such as the index finger of the first hand, may be placed on the translation handle 110 at a same time as the finger 124 and the thumb of the first hand are pinching the grip 112. In these embodiments, the index finger of the first hand may advance the probe 102, while the grip 112 is held between the finger 124 and the thumb of the first hand. In other embodiments, a finger 124 of a second hand of the clinician may be placed on the translation handle 110 at a same time as the finger 124 and the thumb of the first hand are pinching the grip 112. In these embodiments, the finger 124 of the second hand may advance the probe 102, while the grip 112 is held between the finger 124 and the thumb of the first hand.

The doubling, or in some examples, tripling, the length of the probe 102 within the IV device assembly 100 may increase the distance of travel of the probe 102. In the examples where the probe 102 is a patency device, a porous distal end 126 of the patency device may be allowed to pass along a relatively longer fluidic path to the catheter assembly 128 described in connection with FIG. 1 in order to check the patency of the catheter assembly 128. Other devices may also be used that not only allow the probe 102 to extend out of the catheter assembly 128 coupled to the IV device assembly 100 but also travel a distance into and through the patient's blood vessel in order to monitor vitals or complete other medical procedures within the patient's body. In some embodiments, any number of lengths of the probe 102 may be placed within the IV device assembly 100 in order to increase the distance traveled by the probe 102 while not increasing the length of the IV device assembly 100.

In the embodiment shown in FIG. 10A, the support member 104 passes through a support member channel formed through the translation handle 110 and may terminate at a proximal end of the support member 104 at a grip 112. The support member 104 may be used by a clinician or other HCP to secure a position of the IV device assembly 100 while the translation handle 110 is translated along the length of the IV device assembly 100.

In some embodiments described herein the IV device assembly 100 may include a collapsible sleeve 114. The collapsible sleeve 114 may be formed coaxially around a portion of the probe 102 and mechanically coupled to the VAD coupler 106. In some embodiments, the collapsible sleeve 114 may be made of a foldable and pliant material that allows the collapsible sleeve 114 to be collapsed in on itself. In the embodiments described herein, the collapsible sleeve 114 may be mechanically coupled to the translation handle 110. In some embodiments, the collapsible sleeve 114 may be mechanically coupled to a funnel coupler 108 that is coupled to a proximal end of the VAD coupler 106. The funnel coupler 108 may be coupled to the VAD coupler 106 via, for example, using an adhesive or by implementing an ultrasonic welding process.

As described, in some embodiments, the IV device assembly 100 may include a funnel coupler (not shown) that is coupled to a proximal side of the VAD coupler 106. The funnel coupler may include a mechanical channel formed therein to allow the probe 102 to pass therethrough. Additionally, the channel formed in the funnel coupler may include a seal 116. The seal 116 may prevent any fluids present at a distal end of the seal 116 from passing out of a proximal side of the funnel coupler.

During operation of the IV device assembly 100, a clinician or other HCP may mechanically couple the IV device assembly 100 to a VAD via mechanically coupling the VAD coupler 106 to a coupling device of the VAD. In the example where the probe 102 is a patency device, the clinician may choose to mechanically couple the IV device assembly 100 to the VAD a certain interval or during any other patient monitoring process. Although the present specification describes the probe 102 as a patency device, it is to be understood that any type of senor or other device may be used as described herein to provide a number of medical diagnosis or medical treatments.

With the IV device assembly 100 mechanically coupled to the VAD at the VAD coupler 106, the clinician may grip the grip 112 with one hand and grip the translation handle 110 with the other. The clinician may then translate the translation handle 110 towards a distal end of the IV device assembly 100. Because, in the embodiment described in connection with FIG. 1, the support member 104 passes through the translation handle 110 and is mechanically coupled to the grip 112, the translation handle 110 slides along the support member 104. The support member 104 maintains a level of rigidity to the IV device assembly 100 as the translation handle 110 is translated.

FIGS. 10C-10G are front elevation, section views of a support member 104 (at a section view at "B" in FIG. 10B) of an IV device assembly 100 according to some embodiments of the present disclosure. As described herein, the support member 104 may pass through the translation handle 110 and terminate at, in the examples shown in FIGS. 10A and 10B, a grip 112 for the clinician to grasp. The support member channel 150 formed through the translation handle 110 and the support member 104 itself may be keyed such that the support member 104 fits within the support member channel 150 at a certain positional angle and the translation handle 110 is prevented from rotating around the support member 104.

Figure 10C:
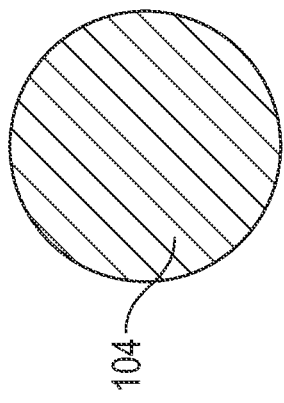
FIG. 10C is a front elevation, section view of a support member of an IV device assembly according to some embodiments of the present disclosure.

In a first example, FIG. 10C shows a support member 104 that has a section view that is circular. Depending on diameter of the support member channel 150 formed in the translation handle 110, the rotation of the translation handle 110 around the support member 104, in this example, may be prevented using a level of interference fitting between the internal diameter of the support member channel 150 and the exterior diameter of the support member 104.

Figure 10D:
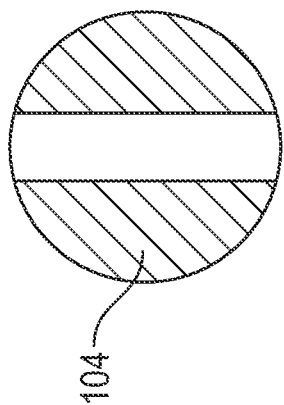
FIG. 10D is a front elevation, section view of a support member of an IV device assembly according to some embodiments of the present disclosure.

In a second example, FIG. 10D shows the support member 104 may have two half moon shapes and a brace formed in the translation handle 110 may be passed between the two half moon shapes. By keying the support member 104 and support member channel 150 this way, the translation handle 110 is prevented from rotating around the support member 104.

Figure 10E:
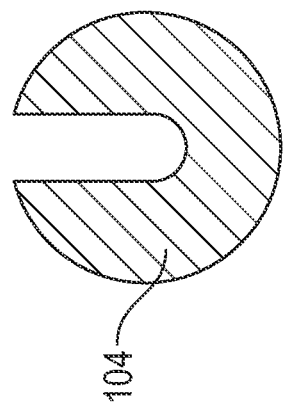
FIG. 10E is a front elevation, section view of a support member of an IV device assembly according to some embodiments of the present disclosure.

In a third example, FIG. 10E shows that the support member 104 may include a notch cut out of it such that the notch interfaces with a finger extending from an internal surface of the support member channel 150. By keying the support member 104 and support member channel 150 this way, the translation handle 110 is prevented from rotating around the support member 104.

Figure 10F:
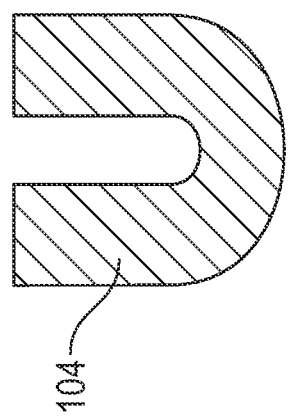
FIG. 10F is a front elevation, section view of a support member of an IV device assembly according to some embodiments of the present disclosure.

In a fourth example, FIG. 10F shows that the support member 104 may be formed to have a "U-shape" cross-section such that a portion of the translation handle 110 may be formed to extend down into the hollow formed in the support member 104. By keying the support member 104 and support member channel 150 this way, the translation handle 110 is prevented from rotating around the support member 104.

Figure 10G:
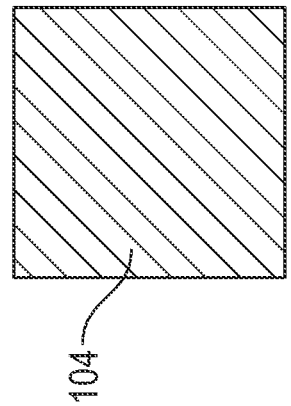
FIG. 10G is a front elevation, section view of a support member of an IV device assembly according to some embodiments of the present disclosure.

In a fifth example, FIG. 10G shows that the support member 104 has a cross-section of a square. The support member channel 150 formed in the translation handle 110 may also be a square so that the support member 104 may pass therethrough. By keying the support member 104 and support member channel 150 this way, the translation handle 110 is prevented from rotating around the support member 104.

Figure 11A:
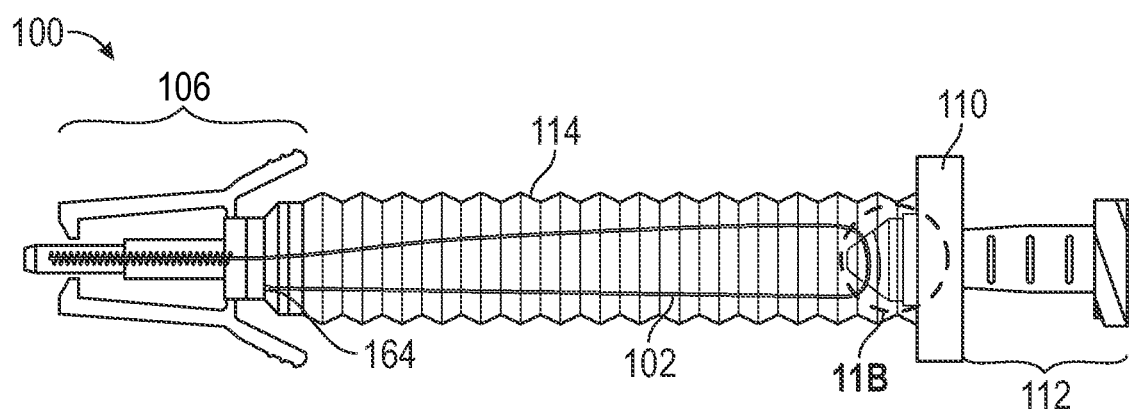
FIG. 11A is a side elevation view of an IV device assembly according to some embodiments of the present disclosure.
Figure 11B:
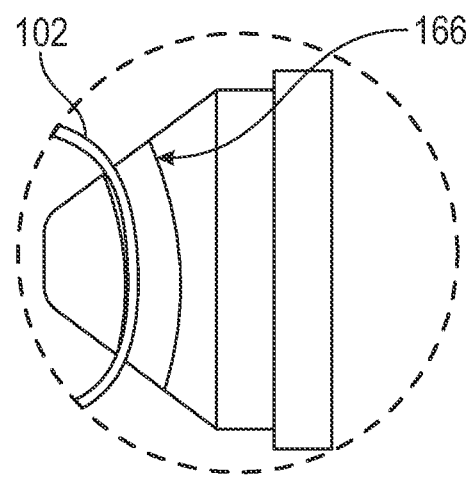
FIG. 11B is a side elevation view of a translation handle of an IV device assembly according to some embodiments of the present disclosure.

FIG. 11A is a side elevation view of an IV device assembly 100 according to some embodiments of the present disclosure. FIG. 11B is a side elevation view of a translation handle 110 of an IV device assembly 100 according to some embodiments of the present disclosure. This embodiment of the IV device assembly 100 shows that the translation handle 110 may include a protruding portion that has the channel 166 formed therethrough. As described herein, the double-length probe 102 may be mechanically coupled to a VAD coupler 106 at an anchor 164 point such that the probe 102 may be passed through the channel 166 and into the channel formed in the VAD coupler 106. Such an arrangement, allows the length of the probe 102 to be doubled within the IV device assembly 100 so that the total length of the IV device assembly 100 may remain the same.

The channel 166 formed in the translation handle 110 may be formed such that the double-length probe 102 may pass through the channel 166 relatively easily. In some embodiments, an interior surface of the channel 166 may be coated with a friction reducing material such as polytetrafluoroethylene.

Figure 12:
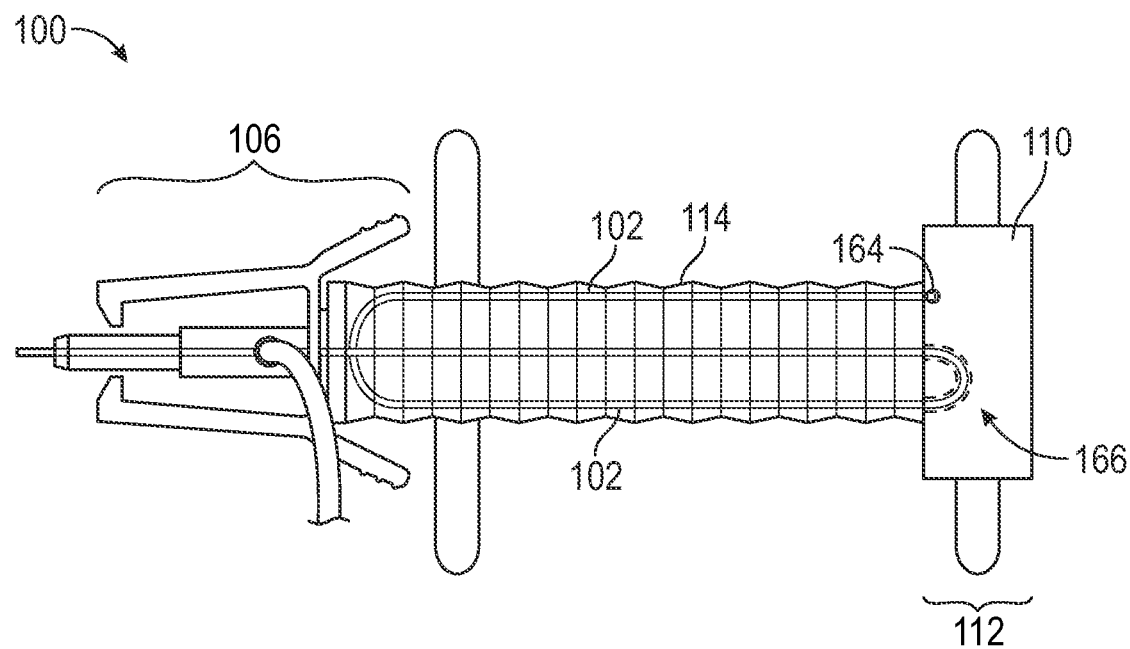
FIG. 12 is a side elevation view of an IV device assembly according to some embodiments of the present disclosure.

FIG. 12 is a side elevation view of an IV device assembly according to some embodiments of the present disclosure. FIG. 12 shows that the probe 102 may be allowed to pass through the interior of the IV device assembly 100 three times. In this embodiment, the anchor 164 may be at the translation handle 110 with the probe 102 passing, loosely, through the IV device assembly 100 and towards the distal end of the IV device assembly 100. The probe 102 may then be allows to pass through a channel 166 as described in connection with FIGS. 11A and 11B before it is directed back distally within the IV device assembly 100 and through the channel formed in the VAD coupler 106.

In this embodiment, the grip 112 may be formed next to the translation handle 110 so that the clinician may operate the IV device assembly 100 with a single hand. Although the embodiments show specific shapes of any of the elements of the IV device assembly 100, it is appreciated that these are merely example shapes and, like the grip 112 and translation handle 110 described in connection with FIG. 12, may be changed in order to facilitate any particular ergonomic fitting. By allowing for a single-handed operation of the IV device assembly 100, the clinician may have a free hand available to concurrently address other devices or instruments associated with the care of the patient.

Figure 13A:
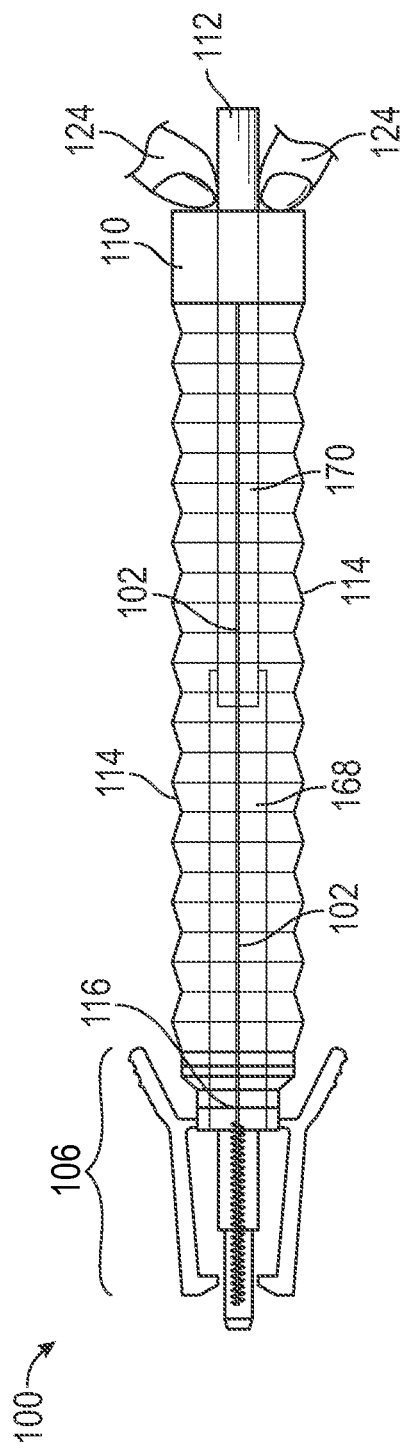
FIG. 13A is a side elevation view of an IV device assembly according to some embodiments of the present disclosure.
Figure 13B:
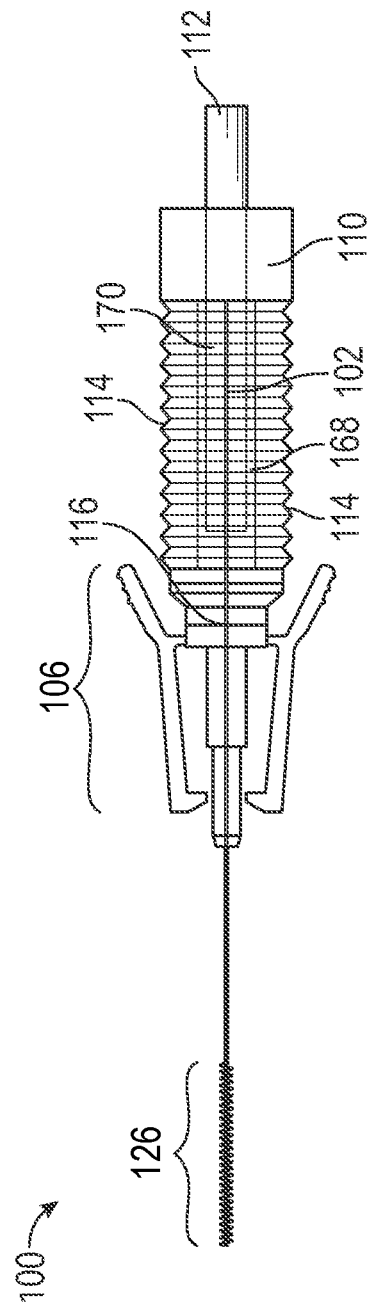
FIG. 13B is a side elevation view of an IV device assembly according to some embodiments of the present disclosure.

FIG. 13A is a side elevation view of an IV device assembly 100 according to some embodiments of the present disclosure. FIG. 13B is a side elevation view of an IV device assembly 100 according to some embodiments of the present disclosure. Similar to other examples described herein, FIG. 13A shows the IV device assembly 100 with a probe 102 in an undeployed state while FIG. 13B shows the IV device assembly 100 with the probe 102 in a deployed or extended state.

In the embodiments shown FIGS. 13A and 13B the support member 104 may include a first sleeve support member 168 and second sleeve support member 170. In this embodiment, an internal diameter of the first sleeve support member 168 may be larger than an outer diameter second sleeve support member 170. During operation, the clinician may, with his or her fingers 124, pass the translation handle 110 towards a distal end of the VAD coupler 106. As this occurs the second sleeve support member 170 may pass, telescopically, into the first sleeve support member 168. Because the probe 102 is placed coaxially within the first sleeve support member 168 and second sleeve support member 170, the probe 102 is advanced while the first sleeve support member 168 and second sleeve support member 170 keep the IV device assembly 100 relatively rigid. The probe 102 may also be prevented from buckling under the force applied to it by the movement of the translation handle 110 by sizing the interior diameter of the second sleeve support member 170. This may allow for the probe 102 to move while also preventing the buckling. Although FIGS. 13A and 13B shows that the support member includes a first sleeve support member 168 and second sleeve support member, the present specification contemplates that the support member may include more than two sleeve support members. In these embodiments, therefore, the plurality of sleeve members may telescope in onto each other such that, during operation, the total length of the IV device assembly 100 is reduced while the probe 102 extends from the distal end of the VAD coupler 106 and into a VAD.

In an embodiment, the IV device assembly 100 may also include the collapsible sleeve 114. The collapsible sleeve 114 may be placed, coaxially, around the first sleeve support member 168, the second sleeve support member 170, and the probe 102. The collapsible sleeve 114 may also be mechanically coupled to the proximal side of the suitable VAD coupler 106 and the distal side of the translation handle 110.

Figure 14:
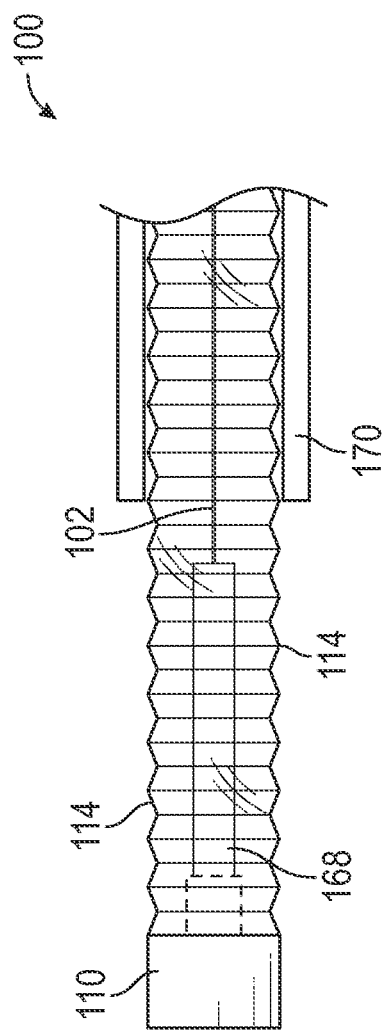
FIG. 14 is a side elevation view of an IV device assembly according to some embodiments of the present disclosure.

FIG. 14 is a side elevation view of an IV device assembly 100 according to some embodiments of the present disclosure. In this embodiment, the second sleeve support member 170 may be formed outside of the collapsible sleeve 114, the first sleeve support member 168, and the probe 102. In this orientation, the collapsible sleeve 114 may hermetically seal the surfaces of the probe 102 while the second sleeve support member 170 and first sleeve support member 168 provide support to the IV device assembly 100 as described.

Figure 15A:
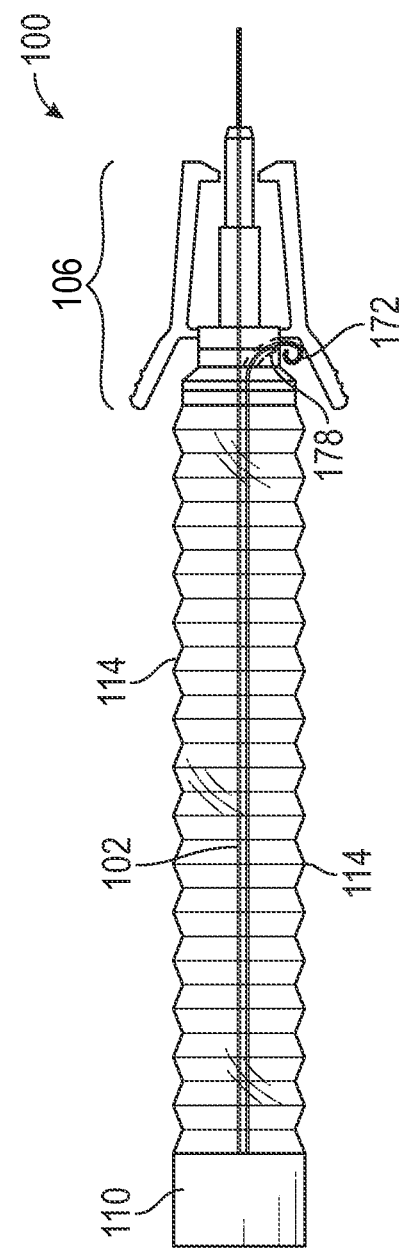
FIG. 15A is a side elevation view of an IV device assembly according to some embodiments of the present disclosure.
Figure 15B:
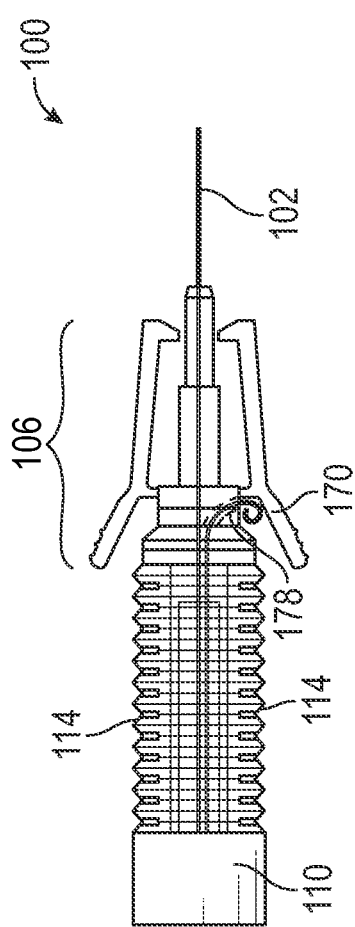
FIG. 15B is a side elevation view of an IV device assembly according to some embodiments of the present disclosure.
Figure 15C:
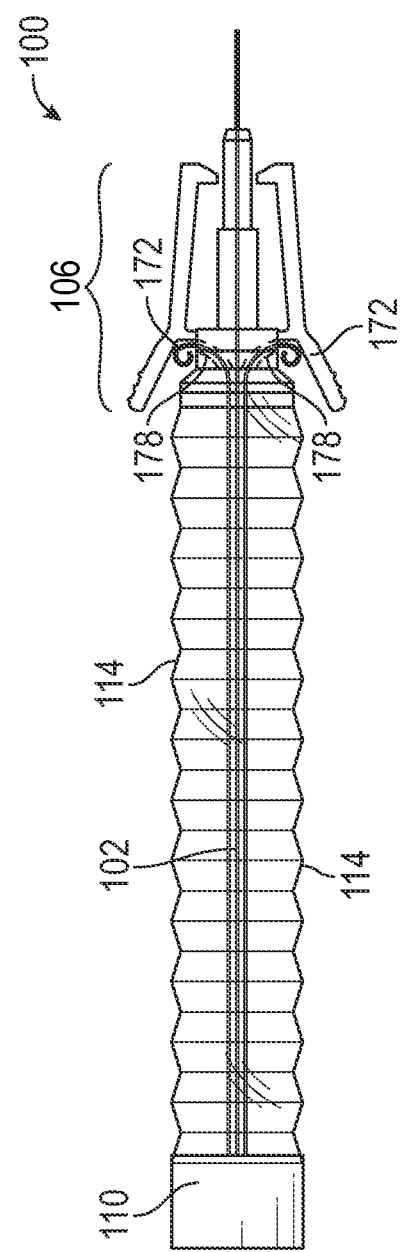
FIG. 15C is a side elevation view of an IV device assembly according to some embodiments of the present disclosure.

FIG. 15A is a side elevation view of an IV device assembly 100 according to some embodiments of the present disclosure. FIG. 15B is a side elevation view of an IV device assembly 100 according to some embodiments of the present disclosure. FIG. 15C is a side elevation view of an IV device assembly 100 according to some embodiments of the present disclosure. These embodiments may each include a suitable VAD coupler 106 formed at distal end of the IV device assembly 100 and a translation handle 110 used to translate the probe 102 through and out of the IV device assembly 100.

The support member 104, in these embodiments, includes one or more bistable springs 172. A bistable spring 172 may be any spring that has two stable equilibrium states such as straight or bent in the embodiments shown. In each of these embodiments, a proximal end of the bistable spring 172 may be mechanically coupled to a distal side of the translation handle 110.

FIG. 15A shows that, as the translation handle 110 is translated towards a distal end of the IV device assembly 100, the support member 104 in the form of the bistable spring 172 is forced through a bistable spring channel 178. The further the translation handle 110 is translated towards the suitable VAD coupler 106, the further the bistable spring 172 extends out of the IV device assembly 100. In some embodiments, owing to the bistable nature of the bistable spring 172, the bistable spring 172 may curl in onto itself. This prevents the bistable spring 172 from proceeding towards other objects near the IV device assembly 100 such as the patient's body. FIG. 15B shows the IV device assembly 100 in a compressed state with the bistable spring 172 fully curled upon itself.

FIG. 15C shows an embodiment where the support member 104 include two bistable springs 172. Again, each bistable spring 172 may be passed through its own bistable spring channel 178 and allowed to curl in onto itself as the translation handle 110 is translated towards the suitable VAD coupler 106.

Figure 16A:
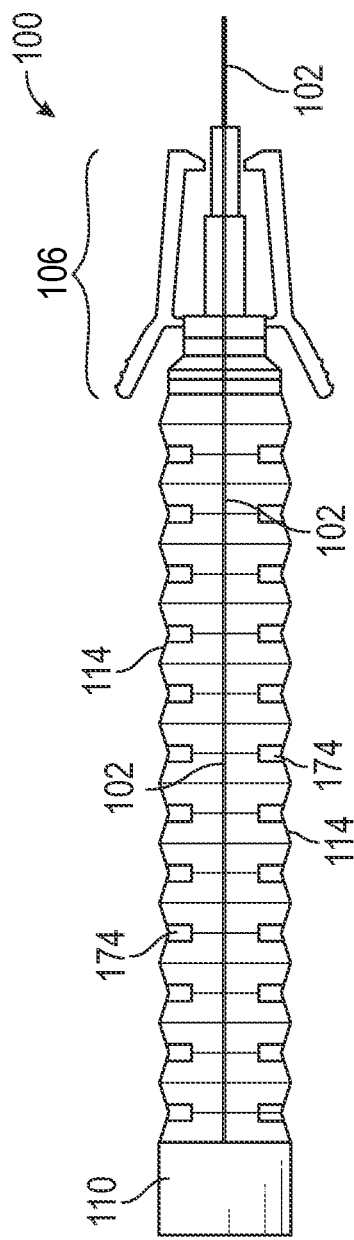
FIG. 16A is a side elevation view of an IV device assembly according to some embodiments of the present disclosure.
Figure 16B:
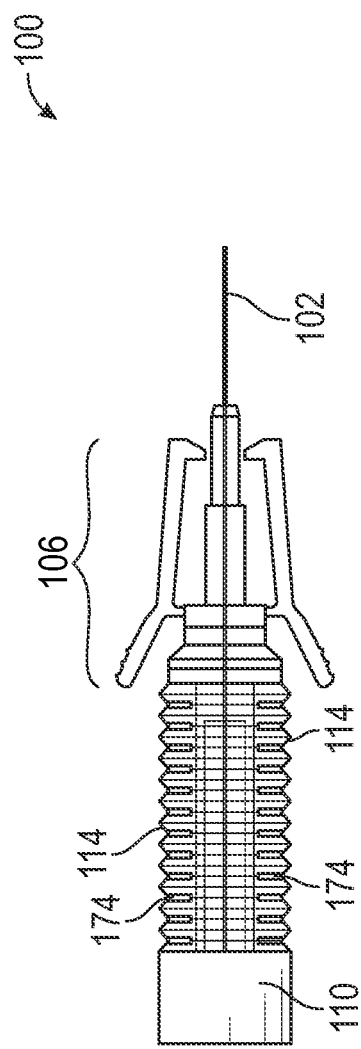
FIG. 16B is a side elevation view of an IV device assembly according to some embodiments of the present disclosure.

FIG. 16A is a side elevation view of an IV device assembly 100 according to some embodiments of the present disclosure. FIG. 16B is a side elevation view of an IV device assembly 100 according to some embodiments of the present disclosure. In this embodiment, a suitable VAD coupler 106 is formed at the distal end of the IV device assembly 100 with a translation handle 110 coupled to the probe 102. The probe 102 may pass into a channel formed in the suitable VAD coupler 106.

The support members in this embodiment may include a plurality of sleeve guides 174. Each sleeve guide 174 may be formed at a crease formed on the collapsible sleeve 114 such that as the translation handle 110 and the probe 102 are advanced, the sleeve guide 174 guide the probe 102 through the IV device assembly 100 and add rigidity to the IV device assembly 100. The sleeve guide 174 may be in to form of an overlayer at the creases that add more structure to the IV device assembly 100.

Figure 17A:
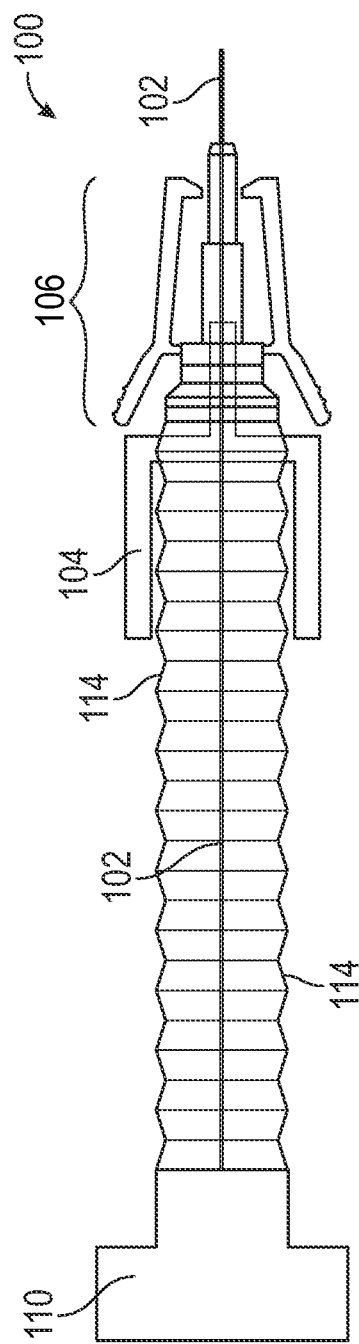
FIG. 17A is a side elevation view of an IV device assembly according to some embodiments of the present disclosure.
Figure 17B:
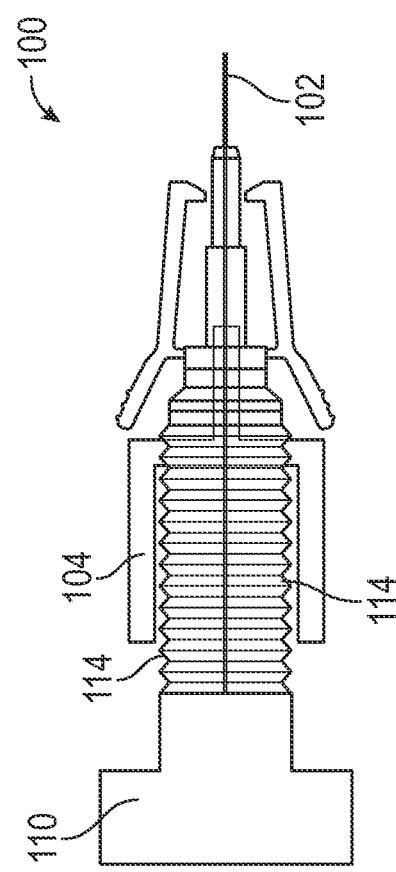
FIG. 17B is a side elevation view of an IV device assembly according to some embodiments of the present disclosure.

FIG. 17A is a side elevation view of an IV device assembly 100 according to some embodiments of the present disclosure. FIG. 17B is a side elevation view of an IV device assembly 100 according to some embodiments of the present disclosure. In this embodiment, a suitable VAD coupler 106 is formed at the distal end of the IV device assembly 100 with a translation handle 110 coupled to the probe 102. The probe 102 may pass into a channel formed in the suitable VAD coupler 106.

FIGS. 17A and 17B show the IV device assembly 100 in an uncompressed and compressed state, relatively. In these embodiments, the support member 104 may consist of a solid wall formed, monolithically, from the suitable VAD coupler 106 and extending, coaxially, down towards a proximal end of the IV device assembly 100. The length of the support member 104 may be sufficient to suit any uses of the IV device assembly 100.

The IV device assembly 100 shown in FIGS. 17A and 17B also show a collapsible sleeve 114 formed coaxially around the probe 102. The collapsible sleeve 114 may be coupled to an interior surface within the support member 104 and at a proximal side of the suitable VAD coupler 106 as well as at a distal side of the translation handle 110.

Figure 18A:
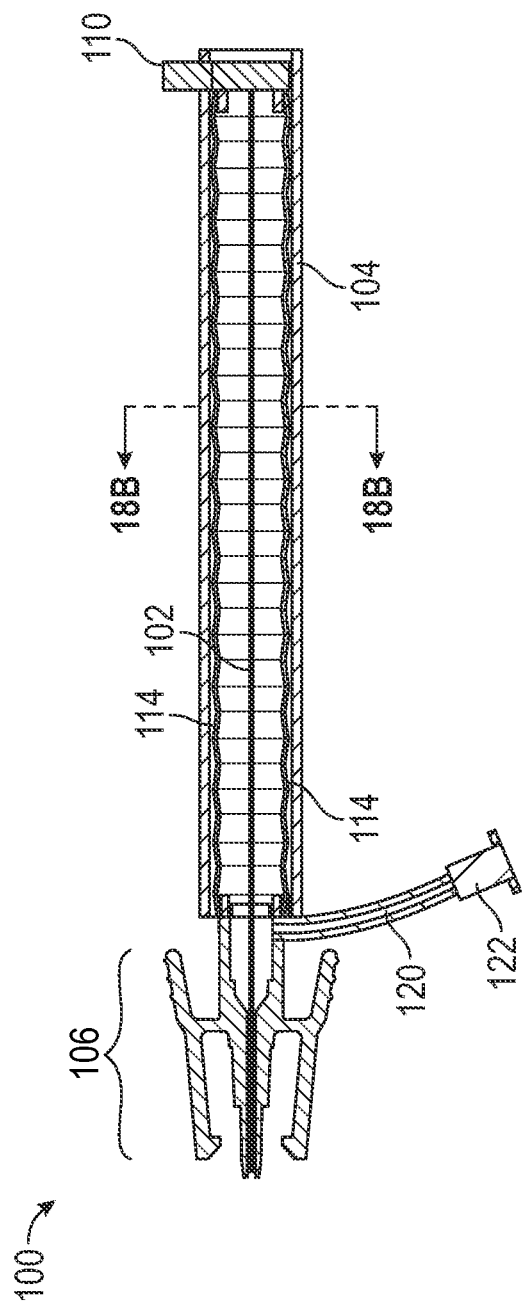
FIG. 18A is a side elevation, section view of an IV device assembly according to some embodiments of the present disclosure.
Figure 18B:
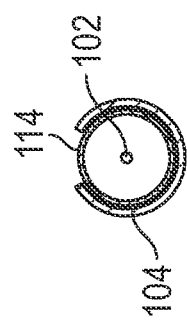
FIG. 18B is a front elevation, section view of a translation handle of an IV device assembly according to some embodiments of the present disclosure.

FIG. 18A is a side elevation, section view of an IV device assembly 100 according to some embodiments of the present disclosure. FIG. 18B is a front elevation, section view of a translation handle 110 of an IV device assembly 100 according to some embodiments of the present disclosure. In these embodiments, the IV device assembly 100 may include a suitable VAD coupler 106 placed at a distal end of the IV device assembly 100. The VAD coupler 106 may include a fluidically coupling port tubing 120 and a port 122 that allows for selective coupling of a blood sample access device or a medication reservoir as described herein.

Similar to FIGS. 17A and 17B, the IV device assembly 100 in FIGS. 18A and 18B include a rigid support member 104 formed around the collapsible sleeve 114 and probe 102. In this embodiment, the support member 104 extends the entire length of the IV device assembly 100 such that the translation handle 110 is placed coaxially inside the support member 104. Again, the support member 104 may be formed, monolithically, during the formation of the suitable VAD coupler 106 in some examples.

The collapsible sleeve 114 may be mechanically coupled to the proximal side of the VAD coupler 106 and to a distal side of the translation handle 110. In order to operate the translation handle 110, the translation handle 110 may have an arm extending therefrom through a slot formed in the support member 104 per FIGS. 18A and 18B. In this embodiment, the probe 102 is completely sealed off from atmosphere via the collapsible sleeve 114 so that no contaminants may interact with a surface of the probe 102.

Figure 19:
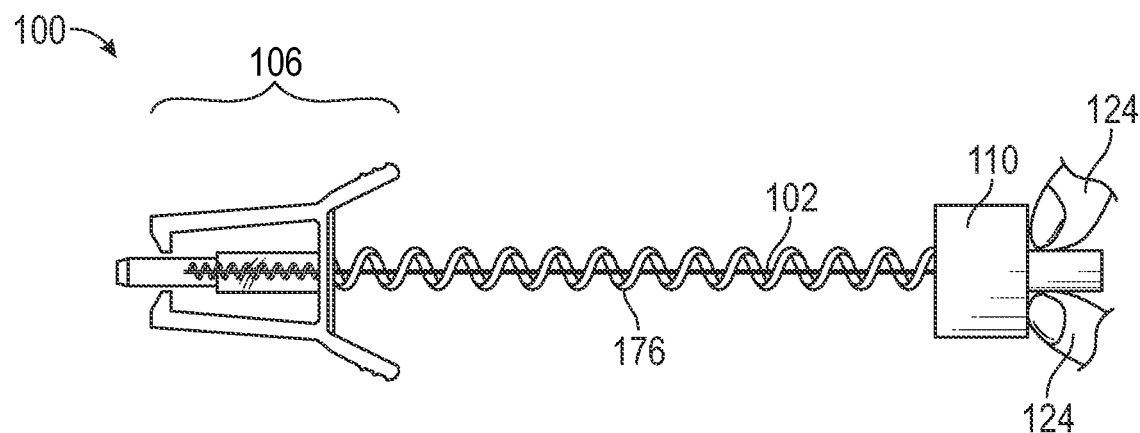
FIG. 19 is a side elevation view of an IV device assembly according to some embodiments of the present disclosure.

FIG. 19 is a side elevation view of an IV device assembly 100 according to some embodiments of the present disclosure. Again, the IV device assembly 100 may include a suitable VAD coupler 106 used to fluidically and mechanically couple the IV device assembly 100 to a VAD. The translation handle may be mechanically coupled to the probe 102 with the probe 102 extending into, at least partially, the channel formed through the VAD coupler 106.

In this embodiment, the support member may include a helical spring 176. The helical spring 176 may be wrapped, coaxially, around the probe 102 from a proximal side of the VAD coupler 106 to the distal side of the translation handle 110. In an embodiment, the helical spring 176 may be coupled mechanically, at a distal end, to the proximal side of the VAD coupler 106. The helical spring 176 may also be mechanically coupled to a distal side of the translation handle 110 at a proximal end of the helical spring 176. The helical spring 176 may be made, in some examples, of a gauge wire that provides sufficient rigidity to the IV device assembly 100 as the clinician uses his or her fingers 124 to move the translation handle 110 distally as described.

Figure 20:
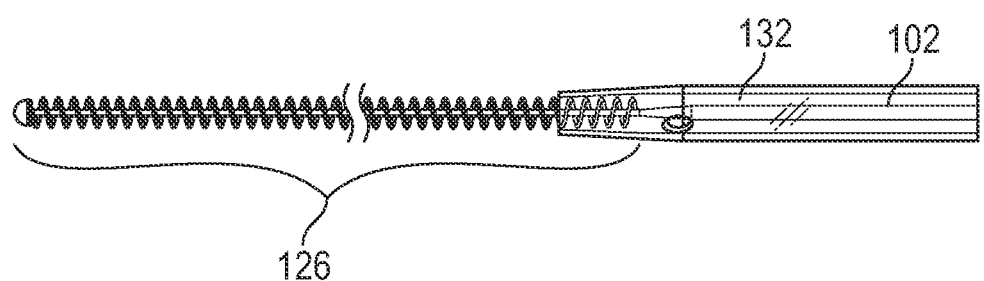
FIG. 20 is a side elevation view of a probe according to some embodiments of the present disclosure.

FIG. 20 is a side elevation view of a probe 102 according to some embodiments of the present disclosure. In some embodiments, the probe 102 may extend through the catheter assembly 128 mechanically and fluidically coupled to the IV device assembly 100 of, for example, FIGS. 1 and 2. The probe 102 is illustrated to be extended slightly past a distal end of the catheter assembly 128 (and specifically the catheter 132) due to the clinician passing the translation handle 110 towards a distal end of the IV device assembly 100 as described herein. As also described herein, the distal end of the probe 102 may include a porous distal end 126. In these embodiments, the probe 102 may be necked down to a smaller diameter and the porous distal end 126 may include a coil winding around the smaller diameter portion of the probe 102. The coil winding is merely one example of what the porous distal end 126 may consist of and the present disclosure contemplates that other porous distal end 126 material may be used.

Additionally, the present disclosure contemplates that certain sensors may be placed within the coil windings or at the very distal end of the probe 102 so that certain physiological characteristics (e.g., vitals) of the patient may be monitored such as blood pressure, pH of the patient's blood, blood chemistry, peripheral capillary oxygen saturation (SP02) levels, blood flow rate, heartbeat, and temperature, among others.

The coil windings illustrated at the porous distal end 126 of the probe 102 are depicted as having a constant pitch across the entire length of the porous distal end 126. However, the present disclosure contemplates that the pitch of the coil windings may vary along the length of the porous distal end 126. The variance in pitch may be a repeating variance, a constant variance or a random variance in order to fit certain patency-checking qualities or other qualities of the probe 102.

The IV device assembly described herein may provide for an integrated extension set in the form of the present IV device assembly with an optimized fluidic resistance that includes a patency improving guidewire instrument that is relatively less traumatic on a patient's blood vessel. The presently described present IV device assembly includes a probe that may be operated using a single hand. The present IV device assembly described herein may be more compact than other extension sets and may combine the patency checking processes with blood sampling processes via use of the blood sample access device for improved workflow and reduce steps and processes in patency checking and blood sampling. Due to the form and components used in the present IV device assembly, the amount of waste may be reduced.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the disclosed embodiments.

The invention claimed is:

1. An IV device assembly, comprising:
a tubing forming a lumen within the IV device assembly, the lumen fluidically coupled to:
a vascular access device (VAD) coupler connectable to a VAD and connected to the tubing; and
an IV device assembly coupler at a proximal end of the tubing;
a probe having a length along the IV device assembly;
a translation handle mechanically coupled to the probe that translates the probe through the VAD coupler and out of a distal end of the IV device assembly, the translation handle comprising a channel formed therethrough for the tubing to pass through as the translation handle is translated towards the distal end of the IV device assembly;
a support member formed along a length of the probe that mechanically supports the probe as it is translated within the IV device assembly; and
a grip formed at a proximal end of the support member, wherein the translation handle is slidable with respect to the support member and the grip.

2. The IV device assembly of claim 1, further comprising a support member channel formed in the translation handle.

3. The IV device assembly of claim 2, wherein the support member is keyed to fit within the support member channel and prevent the support member from rotating about a longitudinal axis of the support member.

4. The IV device assembly of claim 1, wherein the support member is a bistable spring that, as the translation handle is translated towards a distal end of the IV device assembly, exits the VAD coupler through a bistable spring channel and curls upon itself.

5. The IV device assembly of claim 1, wherein the support member comprises a helical spring that wraps around the length of the probe.

6. An IV device assembly, comprising:
a vascular access device (VAD) coupler at a distal end of the IV device assembly that is mechanically couplable to a VAD, the VAD coupler having a channel formed therethrough;
a probe having a length along the IV device assembly;
a translation handle mechanically coupled to the probe via a probe spoke that, as the translation handle is translated, translates the probe through the channel and out of the distal end of the IV device assembly;
a support member formed along a length of the probe that mechanically supports the probe as it is translated within the IV device assembly, the support member comprising a tube formed coaxially around the probe, the tube comprising a slit formed along a longitudinal length of the tube, allowing the probe spoke to pass therethrough;
a tubing forming a fluidic channel within the IV device assembly, wherein the tubing passes through the translation handle such that the translation handle is slidable with respect to the tubing, wherein a distal end of the tubing is attached to the VAD coupler and in fluid communication with the channel, and a proximal end of the tubing is fluidically coupled to an IV device assembly coupler; and
a grip formed at a proximal end of the support member, wherein the translation handle is slidable with respect to the support member and grip.

7. The IV device assembly of claim 6, further comprising a collapsible sleeve formed coaxially around the probe, tube, and tubing.

8. The IV device assembly of claim 7, further comprising a support spring formed within the collapsible sleeve that creates a space between the collapsible sleeve and the probe and biases the translation handle towards a proximal end of the IV device assembly.

9. The IV device assembly of claim 6, further comprising a blood sample access device fluidically and mechanically coupled to the tubing via the IV device assembly coupler.

10. The IV device assembly of claim 6, where in the probe is a guidewire that comprises a porous distal end.

\* \* \* \* \*